(12) United States Patent
Wang et al.

(10) Patent No.: US 6,326,492 B1
(45) Date of Patent: Dec. 4, 2001

(54) HETEROCYCLIC PROTEASE INHIBITORS

(75) Inventors: Aihua Wang, Downingtown; Tianbao Lu; Bruce E. Tomczuk, both of Collegeville, all of PA (US); Richard M. Soll, Lawrenceville, NJ (US); John Spurlino, Downingtown, PA (US); Roger Bone, Bridgewater, NJ (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/578,487

(22) Filed: May 26, 2000

Related U.S. Application Data

(60) Provisional application No. 60/136,386, filed on May 27, 1999.

(51) Int. Cl.[7] .................. C07D 265/02; C07D 213/72
(52) U.S. Cl. .................. 544/63; 546/290; 546/297; 546/304; 546/329; 546/340
(58) Field of Search .................. 546/297, 290, 546/304, 329, 340; 544/63

(56) References Cited

U.S. PATENT DOCUMENTS

| | | | |
|---|---|---|---|
| 4,499,082 | 2/1985 | Shenvi et al. | 514/2 |
| 4,727,064 | 2/1988 | Pitha | 514/58 |
| 4,764,604 | 8/1988 | Müller | 536/103 |
| 5,024,998 | 6/1991 | Bodor | 514/58 |
| 5,466,811 | 11/1995 | Alexander | 546/283 |
| 5,658,885 | 8/1997 | Lee et al. | 514/19 |
| 6,037,356 | 3/2000 | Lu et al. | 514/349 |

FOREIGN PATENT DOCUMENTS

| | | |
|---|---|---|
| 2164684 | 6/1996 | (CA) . |
| 0 363 284 | 4/1990 | (EP) . |
| 0 604 022 | 6/1994 | (EP) . |
| 0 761 251 | 3/1997 | (EP) . |
| WO 95/07291 | 3/1995 | (WO) . |
| WO 96/11668 | 4/1996 | (WO) . |
| WO 96/18644 | 6/1996 | (WO) . |
| 9618644 * | 6/1996 | (WO) . |
| 9701338 * | 6/1996 | (WO) . |
| WO 96/32143 | 10/1996 | (WO) . |
| WO 96/38136 | 12/1996 | (WO) . |
| WO 97/01338 | 1/1997 | (WO) . |
| WO 97/30708 | 8/1997 | (WO) . |
| WO 97/46207 | 12/1997 | (WO) . |
| WO 98/16547 | 4/1998 | (WO) . |
| WO 98/31670 | 7/1998 | (WO) . |

OTHER PUBLICATIONS

Barrett, A.J., "Proteinase inhibitors: potential drugs?" *Enzyme Inhibitors as Drugs*, Sandler, M., ed., The Macmillan Press Ltd., London, England, pp. 219–229 (1980).
Baugh, R.J., and Travis, J., "Human Leukocyte Granule Elastase: Rapid Isolation and Characterization," *Biochemistry* 15:836–841 (1979).
Brown, F.J., et al., "Design of Orally Active, Non–Peptidic Inhibitors of Human Leukocyte Elastase," *J. Med. Chem.* 37:1259–1261 (1994).
Claeson, G., "Synthetic peptides and peptidomimetics as substrates and inhibitors of thrombin and other proteases in the blood coagulation system," *Blood Coagulation and Fibrinolysis* 5:411–436 (1994).
Coughlin, S.R., "Molecular Mechanisms of Thrombin Signaling," *Semin. Hematol.* 31:270–277 (1994).
Cuypers, H.T., et al., "Sulfhydryl Content of Bovine Eye Lens Leucine Aminopeptidase," *J. Biol. Chem.* 257:7086–7091 (1982).
Edwards, P.D., et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole," *J. Amer. Chem. Soc.* 114:1854–1863 (1992).

(List continued on next page.)

*Primary Examiner*—Mukund J. Shah
*Assistant Examiner*—Sudhaker B Patel
(74) *Attorney, Agent, or Firm*—Sterne, Kessler, Goldstein & Fox, P.L.L.C.

(57) ABSTRACT

Described are compounds of the Formula VII:

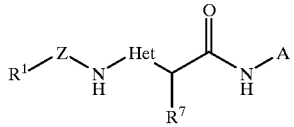

VII wherein Het, $R^1$, $R^7$ and A are set forth in the specification, as well as hydrates, solvates or pharmaceutically acceptable salts thereof, that inhibit proteolytic enzymes such as thrombin. Also described are methods for preparing such compounds. The compounds of the invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin. The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

41 Claims, No Drawings

OTHER PUBLICATIONS

Harker, L.A., "Strategies for inhibiting the effects of thrombin," *Blood Coagulation and Fibrinolysis* 5(*Suppl. 1*):S47–S58 (1994).

Jeong, J.–H., et al., "Cyclic Guanidino–Sugars with low $pK_a$ as Transition–State Analog Inhibitors of Glycosidases: Neutral Instead of Charged Species Are the Active Forms," *J. Am. Chem. Soc. 118*:4227–4234 (1996).

Kim, K.S., et al., "Preparation of Argatroban Analog Thrombin Inhibitors with Reduced Basic Guanidine Moiety, And Studies of Their Cell Permeability and Antithrombotic Activities," *Med. Chem. Res. 6*:377–383 (1996).

Lee, S.–L., et al., "Amidino and guanidino substituted boronic acid inhibitors of trypsin–like enzymes," *CAPLUS Accession No. 1997:594514*, Abstract of U.S. Patent 5,658,885 (1997).

Lefkovits, J., and Topol, E.J., "Direct Thrombin Inhibitors in Cardiovascular Medicine," *Circulation 90*:1522–1536 (1994).

Mack, H., et al., "Design, Synthesis and Biological Activity of Novel Rigid Amidino–Phenylalanine Derivatives as Inhibitors of Thrombin," *J. Enzyme Inhib. 9*:73–86 (1995).

Sauliner, M.G., et al., "An efficient method for the synthesis of guanidino prodrugs," *Bioorg. Med. Chem. Lett. 4*:1985–1990 (1994).

* cited by examiner

HETEROCYCLIC PROTEASE INHIBITORS

This application claims priority benefit of U.S. Provisional Appl. No. 60/136,386, filed May 27, 1999, the contents of which are entirely incorporated by reference herein.

BACKGROUND OF THE INVENTION

1. Field of the Invention

The present invention relates to novel compounds that function as proteolytic enzyme inhibitors, and particularly to a new class of thrombin inhibitors.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

Edwards et al., *J. Amer. Chem. Soc.* 114:1854–63(1992), describes peptidyl α-ketobenzoxazoles that reversibly inhibit the serine proteases human leukocyte elastase and porcine pancreatic elastase.

European Published Application 363 284 describes analogs of peptidase substrates in which the nitrogen atom of the scissile amide group of the substrate peptide has been replaced by hydrogen or a substituted carbonyl moiety.

Australian Published Application 86245677 also describes peptidase inhibitors having an activated electrophilic ketone moiety such as fluoromethylene ketone or α-keto carboxyl derivatives.

Brown et al., *J. Med. Chem.* 37:1259–1261 (1994) describes orally active, non-peptidic inhibitors of human leukocyte elastase which contain trifluoromethylketone and pyridinone moieties.

H. Mack et al., *J. Enzyme Inhibition*, 9:73–86 (1995) describes rigid amidino-phenylalanine thrombin inhibitors which contain a pyridinone moiety as a central core structure.

PCT International Published Application WO 97/01338 describes pyridinone compounds having the formula:

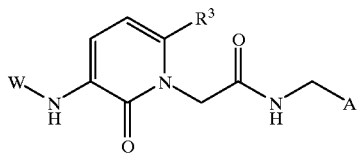

where

W is $R^1$, $R^1OCO$, $R^1CO$, $R^1SO_2$, or $(R^1)_m(CH_2)_nNH_qCO$;

$R^1$ is $R^2(CH_2)_n$, $(R^2)(OR^2)CH(CH_2)_p$, $(R^2)_2CH(CH_2)_n$, and $R^2O(CH_2)_p$;

$R^2$ is hydrogen, optionally substituted phenyl, naphthyl, biphenyl, a mono- or bicyclic heterocyclic ring, $COOR^6$, $C_{1-4}$ linear or branched alkyl, $C_{3-7}$ cycloalkyl, or $C_{7-12}$ bicyclic alkyl;

$R^3$ is hydrogen, $C_{1-4}$ linear or branched alkyl, $C_{3-7}$ cycloalkyl, or trifluoromethyl;

A is one of:

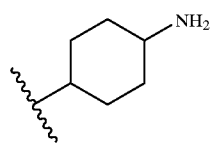

trans

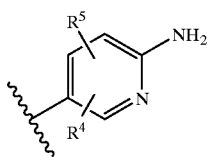

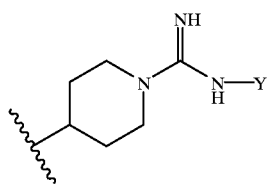

where Y is hydrogen, hydroxy, or CN; and $R^6$ is hydrogen, or $C_{1-4}$ linear or branched alkyl.

PCT International Published Application WO97/30708 discloses pyridinone compounds of the general formula:

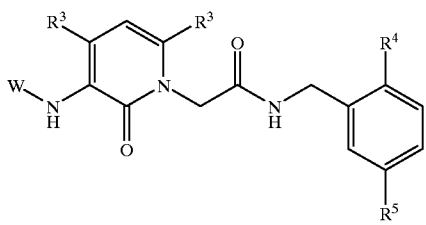

The compounds are disclosed to be useful for inhibiting thrombin and associated thrombotic occlusions.

PCT Published Application WO 96/18644 describes compounds having the formula:

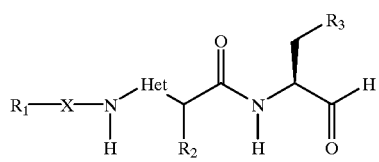

wherein

Het is selected from the group consisting of

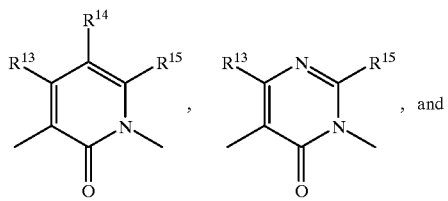

and $R_3$ is selected from the group consisting of:

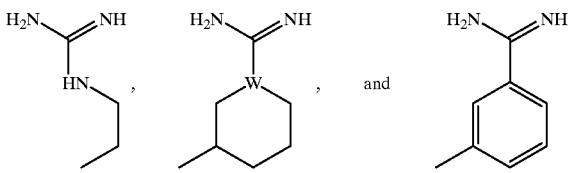

The compounds are described as specific inhibitors of thrombin.

A need continues to exist for additional non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel cyclic oxyguanidine compounds having Formula VII (below). Also provided are processes for preparing compounds of Formula VII. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula VII.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging or thrombi in a mammal.

In another aspect, the present invention includes processes for preparing an oxyguanidine compound of the invention, comprising:

condensing or coupling a compound of formula:

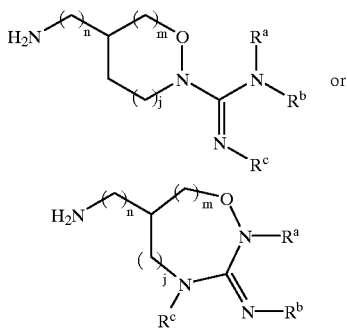

or a salt thereof, with a compound of Formula XI:

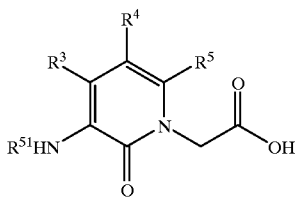

XI where $R^3$, $R^4$, $R^5$, $R^{51}$, $R^a$, $R^b$, $R^c$, n, m and j are as defined herein.

DETAILED DESCRIPTION OF THE PREFERRED EMBODIMENTS

Compounds of the present invention include compounds of Formula VII:

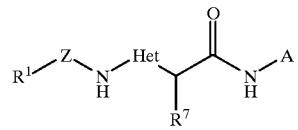

VII or a solvate, hydrate or pharmaceutically acceptable salt thereof; wherein:

A is one of

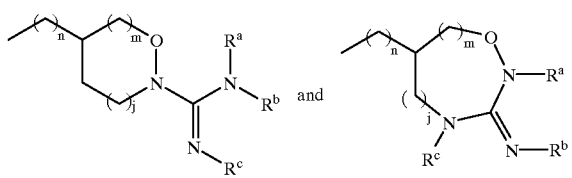

$R^1$ is alkyl, cycloalkyl, cycloalkylalkyl, alkenyl, alkynyl, aryl, aralkyl, heterocycle or heterocycloalkyl, any of which may be optionally substituted;

Z is —$SO_2$—, —OCO—, —CO—, —$NR^2CO$— or a covalent bond, where $R^2$ is hydrogen, alkyl, aralkyl, aryl, hydroxy ($C_{2-10}$) alkyl, amino($C_{2-10}$)alkyl, monoalkylamino ($C_{2-10}$)alkyl, dialkylamino($C_{2-10}$)alkyl or carboxyalkyl;

Het is selected from the group consisting of

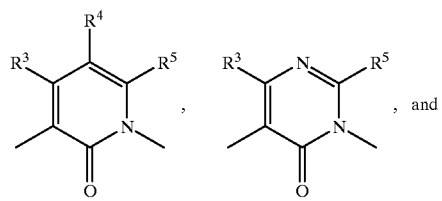

-continued

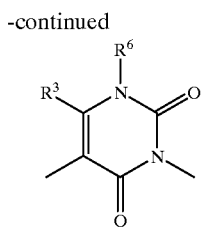

where
R³, R⁴ and R⁵ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —CO$_2$R$^x$, —CH$_2$OR$^x$ or —OR$^x$,
   where R$^x$, in each instance, is independently one of hydrogen, alkyl or cycloalkyl wherein said alkyl or cycloalkyl groups may optionally have one or more unsaturations;
R⁶ is hydrogen, alkyl, aralkyl, aryl, cyano(C$_{2-10}$)alkyl, hydroxy(C$_{2-10}$)alkyl, alkoxy(C$_{2-10}$)alkyl, mono- and di-alkylamino(C$_{2-10}$)alkyl, or carboxyalkyl;
R⁷ is hydrogen, C$_{1-4}$alkyl, or C$_{2-4}$ alkenyl;
R$^a$, R$^b$ and R$^c$ are independently hydrogen, alkyl, hydroxy, alkoxy, aryloxy, aralkoxy, alkoxycarbonyloxy, cyano or —CO$_2$R$^w$, where R$^w$ is alkyl, cycloalkyl, phenyl, benzyl,

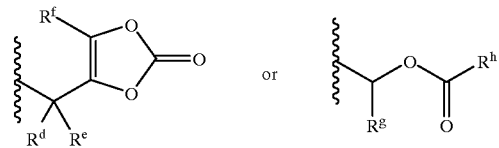

where
R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;
each n is from zero to 4, preferably zero to 2;
each m is from zero to 4, preferably zero to 2; and
each j is zero to 4, preferably zero to 2;
provided that n, m and j are not all zero.

A preferred group of compounds falling within the scope of the present invention include compounds of Formula VII wherein R¹ is one of C$_{6-10}$ ar(C$_{1-4}$) alkyl, C$_{6-10}$ aryl, C$_{4-7}$ cycloalkyl(C$_{1-4}$)alkyl, heterocycle or heterocyclo(C$_{1-4}$)alkyl wherein the heterocycle is a 5- to 7-membered mono- or 9- to 10-membered bi-cyclic heterocyclic ring that can be saturated or unsaturated, which contains 1 to 3 heteroatoms selected from N, O and S. Any of these R¹ groups can be optionally substituted by 1–5, preferably by one, two or three of hydroxy, nitro, trifluoromethyl, halogen, C$_{1-6}$ alkyl, C$_{2-6}$ alkenyl, C$_{6-10}$ aryl, C$_{1-6}$ alkoxy, C$_{6-10}$ ar(C$_{1-6}$)alkoxy, C$_{1-6}$ aminoalkyl, C$_{1-6}$ aminoalkoxy, amino, mono(C$_{1-4}$) alkylamino, di(C$_{1-4}$)alkylamino, C$_{2-6}$ alkylcarbonylamino, C$_{2-6}$ alkoxycarbonylamino, C$_{2-6}$ alkoxycarbonyl, carboxy, C$_{1-6}$ hydroxyalkyl, C$_{2-6}$ hydroxyalkoxy, (C$_{1-6}$)alkoxy(C$_{2-6}$) alkoxy, mono- and di-C$_{1-4}$ alkylamino (C$_{2-6}$)alkoxy, C$_{2-10}$ mono(carboxyalkyl)amino, bis(C$_{2-10}$ carboxyalkyl) amino, C$_{6-14}$ ar(C$_{1-6}$) alkoxycarbonyl, C$_{2-6}$ alkynylcarbonyl, C$_{1-6}$ alkylsulfonyl, C$_{2-6}$ alkenylsulfonyl, C$_{2-6}$ alkynylsulfonyl, C$_{6-10}$ arylsulfonyl, C$_{6-10}$ ar(C$_{1-6}$) alkylsulfonyl, C$_{1-6}$ alkylsulfinyl, C$_{1-6}$ alkylsulfonamido, C$_{6-10}$ arylsulfonamido, C$_{6-10}$ar(C$_{1-6}$) alkylsulfonamido, amidino, guanidino, C$_{1-6}$ alkyliminoamino, formyliminoamino, C$_{2-6}$ carboxyalkoxy, C$_{2-6}$ carboxyalkyl, carboxyalkylamino, cyano, trifluoromethoxy, or perfluoroethoxy.

An especially preferred group of compounds include compounds of Formula VII wherein R¹ is phenyl, benzyl, naphthyl, naphthylmethyl, pyridyl, pyridylmethyl, thienyl, thienylmethyl, quinolinyl or quinolinylmethyl, any of which is optionally substituted by one, two or three optional substituents listed in the preceding paragraph, especially halo, such as chloro or fluoro, methoxy, methyl, trifluoromethyl, cyano, nitro, methylsulfonyl, amino or dimethylamino.

Useful values of R¹ include, for example, benzyl, fluorobenzyl, chlorobenzyl, iodobenzyl, dichlorobenzyl, bromobenzyl, trifluoromethylbenzyl, methylsulfonylbenzyl, di(trifluoromethyl)benzyl, methylbenzyl, t-butylbenzyl, methoxybenzyl, dimethoxybenzyl, hydroxybenzyl, carboxybenzyl, aminobenzyl, methylaminobenzyl, n-butylaminobenzyl, amidinobenzyl, guanidinobenzyl, formyliminoaminobenzyl, acetimidoylaminobenzyl, methoxycarbonylbenzyl, ethoxycarbonylbenzyl, carboxymethoxybenzyl, naphthylmethyl, hydroxynaphthylmethyl, cyclohexylmethyl, cyclopentylmethyl, phenyl, chlorophenyl, iodophenyl, dichlorophenyl, bromophenyl, trifluoromethylphenyl, methylsulfonylphenyl, di(trifluoromethyl)phenyl, methylphenyl, t-butylphenyl, methoxyphenyl, dimethoxyphenyl, hydroxyphenyl, carboxyphenyl, aminophenyl, methylaminophenyl, n-butylaminophenyl, amidinophenyl, guanidinophenyl, formyliminoaminophenyl, acetimidoylaminophenyl, methoxycarbonylphenyl, ethoxycarbonylphenyl, carboxymethoxyphenyl, naphthyl, hydroxynaphthyl, cyclohexyl, and cyclopentyl. Additional useful values include pyridyl, thienyl, isoquinolinyl, pyridylmethyl, isoquinolinylmethyl, tetrahydroquinolinyl and tetrahydroquinolinylmethyl.

More preferred values of R¹ include phenyl, 2-chlorophenyl, 3-chlorophenyl, 4-chlorophenyl, 4-bromophenyl, 4-iodophenyl, 4-methoxyphenyl, 4-methylphenyl, 2-trifluoromethylphenyl, 4-trifluoromethylphenyl, 2-fluorophenyl, 3-fluorophenyl, 4-fluorophenyl, 3,4-dichlorophenyl, 3-chloro-4-fluorophenyl, 3,5-dichlorophenyl, 2-methylphenyl, 3-methylphenyl, 4-ethylphenyl, 2-methylsulfonylphenyl, 4-isopropylphenyl, 3,4-dimethoxyphenyl, 2,4,6-trimethylphenyl, 2,5-dimethylphenyl, 4-vinylphenyl, 2-chloro-6-methylphenyl, 3-bromo-6-methoxyphenyl, 3-chloro-2-methylphenyl, 2-chloro-5-trifluoromethylphenyl, 2,4-dichlorophenyl, 2-butoxy-5-(1,1-dimethylpropyl)phenyl, 3-nitrophenyl, 4-chloro-3-nitrophenyl, 4-methylcarbonylaminophenyl, 4-tert-butylphenyl, 3-cyanophenyl, 4-methylsulfonylphenyl, pentafluorophenyl, 2,5-dichlorophenyl, 2,4-dimethoxyphenyl, 2-methyl-5-nitrophenyl, 3-chloro-2-cyanophenoxy)phenyl, 2-chloro-4-fluorophenyl, 3-chloro-6-methoxyphenyl, 2-methoxy-5-methylphenyl, 4-phenylphenyl, 2-propylbutyl, 5-chloro-2-methoxyphenyl, 2-cyanophenyl, 2-(N-hydroxy)aminophenyl, 2-(4-biphenylmethoxy)phenyl, 2-(3-biphenylmethoxy)phenyl, 2-(phenylsulfonyl)phenyl, 2,4-bis(methylsulfonyl)phenyl, 2-chloro-4-methylsulfonylphenyl, benzyl, 3-chlorobenzyl, 3-trifluoromethylbenzyl, 2-trifluoromethylbenzyl, 2-iodobenzyl, 2-chlorobenzyl, 2-bromobenzyl, 3-fluorobenzyl, 4-chlorobenzyl, 2-chloro-6-fluorobenzyl, 2-fluorobenzyl, 2,3-dichlorobenzyl, 3,4-difluorobenzyl, 2,4-dichlorobenzyl, 2,5-dichlorobenzyl, 3,4-dichlorobenzyl, 2-methylbenzyl, 5-chloro-2-methoxybenzyl, 2-cyanobenzyl, 2-(4-biphenylmethoxy)benzyl, 2-(3-biphenylmethoxy)benzyl, 2-(phenylsulfonyl)benzyl, 2,4-bis (methylsulfonyl)benzyl, 3-methylsulfonylbenzyl, 2-chloro-4-methylsulfonylbenzyl, 1-naphthalenylmethyl, 2-naphthalenylmethyl, and 2-naphthalenyl.

Additional preferred values of $R^1$ include dansyl, thien-2-yl, pyridin-2-yl, 3-methylquinolin-1-yl, 1-methylimidazol-4-yl, quinolin-5-yl, quinoline-8-yl, 6-bromonaphthalen-2-yl, 6-chloronaphthalen-2-yl, 5-chlorothien-2-yl, 5-methyl-8-quinolinyl, 8-quinolinylmethyl, 5-methyl-8-quinolinylmethyl, 4-benzo-2,1,3-thiadiazolyl, and 5-chloro-1,3-dimethyl-4-pyrazolyl.

Preferred values of $R^2$ in Formula VII include hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, $C_{2-7}$ carboxyalkyl, mono ($C_{1-4}$ alkyl)amino($C_{1-8}$)alkyl, and di($C_{1-4}$ alkyl)amino($C_{1-8}$) alkyl. Suitable values of $R^2$ include hydrogen, methyl, ethyl, propyl, n-butyl, benzyl, phenylethyl, 2-hydroxyethyl, 3-hydroxypropyl, 4-hydroxybutyl, 2-aminoethyl, 2-carboxymethyl, 3-carboxyethyl, 4-carboxypropyl and 2-(dimethylamino)ethyl, with hydrogen being most preferred.

Preferred Het groups include

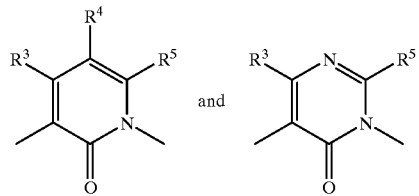

and

Preferred compounds are those where $R^3$, $R^4$ and $R^5$ are independently hydrogen, $C_{1-4}$ alkyl, $C_{3-7}$ cycloalkyl, $C_{6-14}$ aryl, especially $C_{6-10}$ aryl, $C_{6-10}$ ar($C_{1-4}$)alkyl, trifluoromethyl, halogen, hydroxyalkyl, cyano, nitro, carboxamido, carboxy, alkoxycarbonyl, carboxymethyl, alkoxycarbonylmethyl, or cycloalkyloxycarbonyl.

Useful values of $R^3$, $R^4$ and $R^5$ include hydrogen, methyl, ethyl, propyl, chloro, bromo, trifluoromethyl, hydroxymethyl, methoxy, ethoxy, carboxamido, nitro, phenyl, cyclopropyl, hydroxy, isopropyl, methoxycarbonyl, ethoxycarbonyl and benzyl.

Preferred $R^5$ groups include hydrogen, halogen, $C_{1-5}$ alkyl, $C_{3-6}$ alkenyl, $C_{3-5}$ cycloalkyl, trifluoromethyl, and $C_{1-4}$ alkoxy, more preferably $C_{1-4}$ alkyl, such as methyl, ethyl, propyl or isopropyl.

A particularly preferred Het, when $R^3$ and $R^4$ are independently selected to be hydrogen or methyl, is

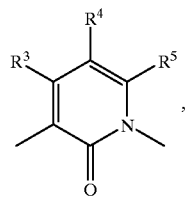

wherein $R^5$ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, and S-3-hexyl. A particularly preferred Het according to this aspect has hydrogen, methyl, ethyl, propyl or isopropyl as $R^5$.

Preferred values of Z include —$SO_2$— and a covalent bond.

A preferred $R^7$ group is hydrogen.

Preferred values of $R^a$, $R^b$ and $R_c$ in Formula VII are independently hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

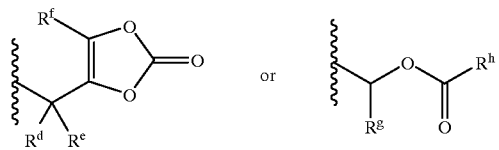

where $R^d$–$R^h$ are defined as above. When $R^a$, $R^b$ and $R^c$ are —$CO_2R^w$, where $R^w$ is one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

According to a particularly preferred aspect, provided are compounds of Formula VII wherein Z is —$SO_2$—, $R^1$ is substituted or unsubstituted aryl or aralkyl, Het is

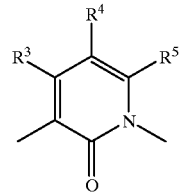

and $R^a$, $R^b$ and $R^c$ are all hydrogen. A very preferred aspect is directed to such compounds where $R^1$ is substituted or unsubstituted benzyl or phenyl, and $R^a$, $R^b$ and $R^c$ are all hydrogen.

A preferred group of compounds has Formula VIII:

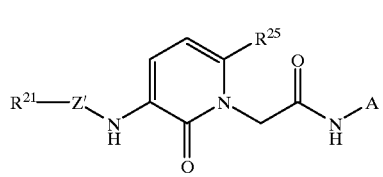

VIII or a solvate, hydrate of pharmaceutically acceptable salt thereof; wherein

Z' is —OCO—, —CO—, —$SO_2$—, —NHCO—, or a covalent bond;

$R^{21}$ is $R^{22}(CH_2)_k$, where k is 0–4, $(R^{22})(OR^{22})CH(CH_2)_p$, where p is 1–4, $(R^{22})_2CH(CH_2)_k$, where k is 0–4 and $R^{22}$ can be the same or different, and wherein $(R^{22})_2$ can also be a ring substituent on CH represented by $C_{3-7}$ cycloalkyl, $C_{7-12}$ bicyclic alkyl, or a 5- to 7- membered mono-, or 9- to 10-membered bicyclic heterocyclic ring which can be saturated or unsaturated, and which contains from one to three heteroatoms selected from the group consisting of N, O and S, and $R^{22}O(CH_2)_p$, wherein p is 1–4;

$R^{22}$ is hydrogen; phenyl, unsubstituted or substituted with one or more of $C_{1-4}$ alkyl, $C_{1-4}$ alkoxy, halogen, trifluoromethyl, hydroxy, COOH, or $CONH_2$; naphthyl; biphenyl; a 5- to 7- membered mono- or a 9- to 10-membered bicyclic heterocyclic ring which can be saturated or unsaturated, and which contains from one to three heteroatoms selected from the group consisting of N, O and S; $C_{1-4}$ alkyl; $C_{3-7}$ cycloalkyl, or $C_{7-12}$ bicyclic alkyl;

$R^{25}$ is hydrogen, $C_{1-4}$ alkyl $C_{3-7}$ cycloalkyl, or trifluoromethyl;

$R^a$, $R^b$ and $R^c$ are independently hydrogen, alkyl, hydroxy, alkoxy, aryloxy, aralkoxy, alkoxycarbonyloxy, cyano or $-CO_2R^w$, where $R^w$ is alkyl, cycloalkyl, phenyl, benzyl,

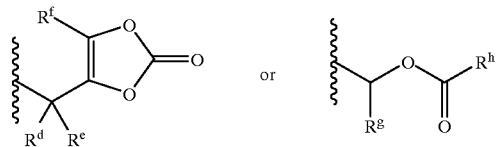

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 4;

m is zero to 2; and j is zero to 2.

A useful class of compounds is the embodiment wherein Z' is a covalent bond or $-SO_2-$. A further useful subclass of compounds is the embodiment wherein $R^{21}$ is $R^{22}(CH_2)_k$, $(R^{22})_2CH(CH_2)_k$, phenyl, or $(phenyl)_2-CH$.

Another useful class of compounds is the embodiment wherein $R^{25}$ is $C_{1-4}$ alkyl and particularly wherein $R^{25}$ is methyl, ethyl, propyl or isopropyl.

Exemplary structures of compounds within the scope of the invention include the following

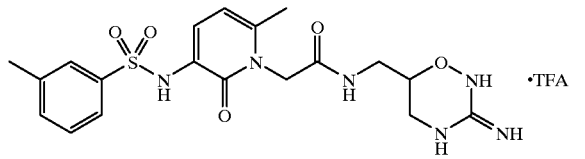

N-[(3-imino(1,2,4-oxadiazaperhydroin-6-yl))methyl]-2-(6-methyl-3-{[(3-methylphenyl)sulfonyl]amino}-2-oxohydropyridyl)acetamide trifluoroacetate; and

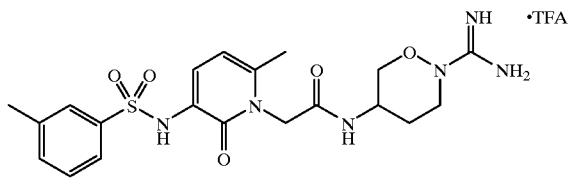

5-[2-(6-methyl-3-{[(3-methylphenyl)sulfonyl]amino)-2-oxohydropyridyl) acetylamino]-1,2-oxazaperhydroine-2-carboxamidine trifluoroacetate;

as well as pharmaceutically acceptable salts thereof, for example the hydrochloride, trifluoroacetate and acetate salts thereof. Compounds of the above formulae were found to inhibit thrombin protease with inhibitory activities of 26 and 0.38 nM, respectively.

Useful compounds of the present invention include:

5-[2-(6-methyl-3-{benzylsulfonylamino}-2-oxohydropyridyl)acetylamino]-1,2-oxazaperhydroine-2-carboxamidine;

5-[2-({3-benzylsulfonylamino}-2-oxohydropyridyl)acetylamino]-1,2-oxazaperhydroine-2-carboxamidine;

5-[2-(6-methyl-3-{benzylsulfonylamino }-2-oxohydropyridyl)acetylamino]-1,2-oxazaperhydroine-2-carboxamidine;

5-[2-(6-methyl-3-{(3-methylphenyl)sulfonylamino}-2-oxohydropyridyl)acetylamino]-1,2-oxazaperhydroine-2-carboxamidine;

5-[2-(6-methyl-3-{benzyloxycarbonylamino}-2-oxohydropyridyl)acetylamino]-1,2-oxazaperhydroine-2-carboxamidine;

5-[2-(6-methyl-3-{3-chlorobenzylsulfonylamino}-2-oxohydropyridyl)acetylamino]-1,2-oxazaperhydroine-2-carboxamidine;

5-[2-(6-methyl-3-{3-tuifluoromethylbenzylsulfonylamino}-2-oxohydropyridyl)acetylamino]-1,2-oxazaperhydroine-2-carboxamidine;

5-[2-(6-methyl-3-2-iodobenzylsulfonylamino}-2-oxohydropyridyl)acetylamino]-1,2-oxazaperhydroine-2-carboxamidine;

5-[2-(6-methyl-3-{2-chlorobenzylsulfonylamino}-2-oxohydropyridyl)acetylamino]-1,2-oxazaperhydroine-2-carboxamidine;

5-[2-(6-methyl-3-{2-bromobenzylsulfonylamino}-2-oxohydropyridyl)acetylamino]-1,2-oxazaperhydroine-2-carboxamidine;

5-[2-(6-methyl-3-{3-fluorobenzylsulfonylamino}-2-oxohydropyridyl)acetylamino]-1,2-oxazaperhydroine-2-carboxamidine;

5-[2-(6-methyl-3-{4-chlorobenzylsulfonylamino}-2-oxohydropyridyl)acetylamino]-1,2-oxazaperhydroine-2-carboxamidine;

5-[2-(6-methyl-3-{2-chloro-6-fluorobenzylsulfonylamino}-2-oxohydropyridyl)acetylamino]-1,2-oxazaperhydroine-2-carboxamidine;

5-[2-(6-methyl-3-{2-fluorobenzylsulfonylamino}-2-oxohydropyridyl)acetylamino]-1,2-oxazaperhydroine-2-carboxamidine;

5-[2-(6-methyl-3-{2,3-dichlorobenzylsulfonylamino}-2-oxohydropyridyl)acetylamino]-1,2-oxazaperhydroine-2-carboxamidine;

5-[2-(6-methyl-3-{3,4-difluorobenzylsulfonylamino}-2-oxohydropyridyl)acetylamino]-1,2-oxazaperhydroine-2-carboxamidine;

5-[2-(6-methyl-3-{2,4-dichlorobenzylsulfonylamino}-2-oxohydropyridyl)acetylamino]-1,2-oxazaperhydroine-2-carboxamidine;
5-[2-(6-methyl-3-{3-chlorophenylsulfonylamino}-2-oxohydropyridyl)acetylamino]-1,2-oxazaperhydroine-2-carboxamidine;
5-[2-(6-methyl-3-{(3-bromophenyl)sulfonylamino}-2-oxohydropyridyl)acetylamino]-1,2-oxazaperhydroine-2-carboxamidine;
5-[2-(6-methyl-3-{(3-fluorophenyl)sulfonylamino}-2-oxohydropyridyl)acetylamino]-1,2-oxazaperhydroine-2-carboxamidine;
5-[2-(6-methyl-3-{naphthalen-1-ylsulfonylamino}-2-oxohydropyridyl)acetylamino]-1,2-oxazaperhydroine-2-carboxamidine;
5-[2-(6-methyl-3-{naphthalen-2-ylsulfonylamino}-2-oxohydropyridyl)acetylamino]-1,2-oxazaperhydroine-2-carboxamidine;
5-[2-(6-methyl-3-{(2-chlorophenyl)sulfonylamino}-2-oxohydropyridyl)acetylamino]-1,2-oxazaperhydroine-2-carboxamidine;
5-[2-(6-methyl-3-{(4-chlorophenyl)sulfonylamino}-2-oxohydropyridyl)acetylamino]-1,2-oxazaperhydroine-2-carboxamidine;
5-[2-(6-methyl-3-{phenylsulfonylamino}-2-oxohydropyridyl)acetylamino]-1,2-oxazaperhydroine-2-carboxamidine;
5-[2-(6-methyl-3-{naphthalen-1-ylmethylsulfonylamino}-2-oxohydropyridyl)acetylamino]-1,2-oxazaperhydroine-2-carboxamidine;
5-[2-(6-methyl-3-{naphthalen-2-ylmethylsulfonylamino}-2-oxohydropyridyl)acetylamino]-1,2-oxazaperhydroine-2-carboxamidine;
5-[2-(6-methyl-3-{(4-bromophenyl)sulfonylamino}-2-oxohydropyridyl)acetylamino]-1,2-oxazaperhydroine-2-carboxamidine;
5-[2-(6-methyl-3-{(4-fluorophenyl)sulfonylamino}-2-oxohydropyridyl)acetylamino]-1,2-oxazaperhydroine-2-carboxamidine;
5-[2-(6-methyl-3-{(4-iodophenyl)sulfonylamino}-2-oxohydropyridyl)acetylamino]-1,2-oxazaperhydroine-2-carboxamidine;
5-[2-(6-methyl-3-{(4-methoxyphenyl)sulfonylamino}-2-oxohydropyridyl)acetylamino]-1,2-oxazaperhydroine-2-carboxamidine;
5-[2-(6-methyl-3-{(3-trifluoromethylphenyl)sulfonylamino}-2-oxohydropyridyl)acetylamino]-1,2-oxazaperhydroine-2-carboxamidine;
5-[2-(6-methyl-3-{(4-isopropylphenyl)sulfonylamino}-2-oxohydropyridyl)acetylamino]1,2-oxazaperhydroine-2-carboxamidine;
5-[2-(6-methyl-3-{(3,4-dimethoxyphenyl)sulfonylamino}-2-oxohydropyridyl)acetylamino]-1,2-oxazaperhydroine-2-carboxamidine;
5-[2-(6-methyl-3-{thien-2-ylsulfonylamino}-2-oxohydropyridyl)acetylamino]-1,2-oxazaperhydroine-2-carboxamidine;
5-[2-(6-methyl-3-{(4-vinylphenylsulfonyl)amino}-2-oxohydropyridyl)acetylamino]-1,2-oxazaperhydroine-2-carboxamidine;
5-[2-(6-methyl-3-{(2-butoxy-5-(1,1-dimethylpropyl)phenylsulfonyl)amino}-2-oxohydropyridyl)acetylamino]-1,2-oxazaperhydroine-2-carboxamidine;
5-[2-(6-methyl-3-{(3-nitrophenyl)sulfonylamino}-2-oxohydropyridyl)acetylamino]-1,2-oxazaperhydroine-2-carboxamidine;
5-[2-(6-methyl-3-{(4-methylcarbonylaminophenyl)sulfonylamino}-2-oxohydropyridyl)acetylamino]-1,2-oxazaperhydroine-2-carboxamidine;
5-[2-(6-methyl-3-{(4-tert-butylphenyl)sulfonylamino}-2-oxohydropyridyl)acetylamino]-1,2-oxazaperhydroine-2-carboxamidine;
5-[2-(6-methyl-3-{(3-cyanophenyl)sulfonylamino}-2-oxohydropyridyl)acetylamino]-1,2-oxazaperhydroine-2-carboxamidine;
5-[2-(6-methyl-3-{(4-methylsulfonylphenyl)sulfonylamino}-2-oxohydropyridyl)acetylamino]-1,2-oxazaperhydroine-2-carboxamidine;
5-[2-(6-methyl-3-{dansylamino}-2-oxohydropyridyl)acetylamino]-1,2-oxazaperhydroine-2-carboxamidine;
5-[2-(6-methyl-3-{pentafluorophenyl)sulfonylamino }-2-oxohydropyridyl)acetylamino]-1,2-oxazaperhydroine-2-carboxamidine;
5-[2-(6-methyl-3-{(2-methoxy-5-methylphenyl)sulfonylamino}-2oxohydropyridyl)acetylamino]-1,2-oxazaperhydroine-2-carboxamidine;
5-[2-(6-methyl-3-{(4-phenylphenyl)sulfonylamino}-2-oxohydropyridyl)acetylamino]-1,2-oxazaperhydroine-2-carboxamidine;
5-[2-(6-methyl-3-{(5-chlorothien-2-yl)sulfonylamino}-2-oxohydropyridyl)acetylamino]1,2-oxazaperhydroine-2-carboxamidine;
5-[2-(6-methyl-3-{quinolin-8-ylsulfonylamino}-2-oxohydropyridyl)acetylamino]-1,2-oxazaperhydroine-2-carboxamidine;
5-[2-(6-methyl-3-{quinolin-5-ylsulfonylamino}-2-oxohydropyridyl)acetylamino]-1,2-oxazaperhydroine-2-carboxamidine;
5-[2-(6-methyl-3-{1-methylimidazol-4-ylsulfonylamino}2-oxohydropyridyl)acetylamino]-1,2-oxazaperhydroine-2-carboxamidine;
5-[2-(6-methyl-3-{3-methylquinolin-8-ylsulfonylamino}-2-oxohydropyridyl)acetylamino]-1,2-oxazaperhydroine-2-carboxamidine;
5-[2-(6-methyl-3-{pyridin-2-ylsulfonylamino}-2-oxohydropyridyl)acetylamino]-1,2-oxazaperhydroine-2-carboxamidine;
5-[2-(6-methyl-3-{pylidin-3-ylsulfonylamino}-2-oxohydropyridyl)acetylamino]-1,2-oxazaperhydroine-2-carboxamidine;
5-[2-(6-isopropyl-3-{-3-methylphenylsulfonylamino}-2-oxohydropyridyl)acetylamino]-1,2-oxazaperhydroine-2-carboxamidine;
5-[2-(6-ethyl-3-{3-methylphenylsulfonylamino}-2-oxohydropyridyl)acetylamino]-1,2-oxazaperhydroine-2-carboxamidine;
5-[2-(6-propyl-3-{3-methylphenylsulfonylamino}-2-oxohydropyridyl)acetylamino]-1,2-oxazaperhydroine-2-carboxamidine;

as well as solvates, hydrates or pharmaceutically acceptable salts (for example, trifluoroacetate and hydrochloride salts) thereof.

Additional useful compounds of the present invention include:

N-[3-imino-(1,2,4-oxadiazaperhydroin-6-yl)methyl]-2-(6-methyl-3-{benzylsulfonylamino}-2-oxohydropyridyl)acetamide;
N-[3-imino-(1,2,4-oxadiazaperhydroin-6-yl)methyl]-2-({3-benzylsulfonylaminol}-2-oxohydropyridyl)acetamide;
N-[3-imino-(1,2,4-oxadiazaperhydroin-6-yl)methyl]-2-(6-methyl-3-{benzylsulfonylamino}-2-oxohydropyridyl)acetamide;
N-[3-imino-(1,2,4-oxadiazaperhydroin-6-yl)methyl]-2-(6-methyl-3-{(3-methylphenyl)sulfonylamino}-2-oxohydropyridyl)acetamide;

N-[3-imino-(1,2,4-oxadiazaperhydroin-6-yl)methyl]-2-(6-methyl-3-{benzyloxycarbonylamino}-2-oxohydropyridyl)acetamide;

N-[3-imino-(1,2,4-oxadiazaperhydroin-6-yl)methyl]-2-(6-methyl-3-{3-chlorobenzylsulfonylamino}-2-oxohydropyridyl)acetamide;

N-[3-imino-(1,2,4-oxadiazaperhydroin-6-yl)methyl]-2-(6-methyl-3-{3-trifluoromethylbenzylsulfonylamino}-2-oxohydropyridyl)acetamide;

N-[3-imino-(1,2,4-oxadiazaperhydroin-6-yl)methyl]-2-(6-methyl-3-{2-iodobenzylsulfonylamino}-2-oxohydropyridyl)acetamide;

N-[3-imino-(1,2,4-oxadiazaperhydroin-6-yl)methyl]-2-(6-methyl-3-{2-chlorobenzylsulfonylamino}-2-oxohydropyridyl)acetamide;

N-[3-imino-(1,2,4-oxadiazaperhydroin-6-yl)methyl]-2-(6-methyl-3-{2-bromobenzylsulfonylamino}-2-oxohydropyridyl)acetamide;

N-[3-imino-(1,2,4-oxadiazaperhydroin-6-yl)methyl]-2-(6-methyl-3-{3-fluorobenzylsulfonylamino}-2-oxohydropyridyl)acetamide;

N-[3-imino-(1,2,4-oxadiazaperhydroin-6-yl)methyl]-2-(6-methyl-3-{4-chlorobenzylsulfonylamino}-2-oxohydropyridyl)acetamide;

N-[3-imino-(1,2,4-oxadiazaperhydroin-6-yl)methyl]-2-(6-methyl-3-{2-chloro-6-fluorobenzylsulfonylamino}-2-oxohydropyridyl)acetamide;

N-[3-imino-(1,2,4-oxadiazaperhydroin-6-yl)methyl]-2-(6-methyl-3-{2-fluorobenzylsulfonylamino}-2-oxohydropyridyl)acetamide;

N-[3-imino-(1,2,4-oxadiazaperhydroin-6-yl)methyl]-2-(6-methyl-3-{2,3-dichlorobenzylsulfonylamino}-2-oxohydropyridyl)acetamide;

N-[3-imino-(1 2,4-oxadiazaperhydroin-6-yl)methyl]-2-(6-methyl-3-{3,4-difluorobenzylsulfonylamino}-2-oxohydropyridyl)acetamide;

N-[3-imino-(1 2,4-oxadiazaperhydrion-6-yl)methyl]-2-(6-methyl-3-{2,4-dichlorobenzylsuffonylamino}-2-oxohydropyridyl)acetamide;

N-[3-imino-(1,2,4-oxadiazaperhydroin-6-yl)methyl]-2-(6-methyl-3-{3-chlorophenylsulfonylamino}-2-oxohydropyridyl)acetamide;

N-[3-imino-(1,2,4-oxadiazaperhydroin-6-yl)methyl]-2-(6-methyl-3-{(3-bromophenyl)sulfonylamino}-2-oxohydropyridyl)acetamide;

N-[3-imino-(1,2,4-oxadiazaperhydroin-6-yl)methyl]-2-(6-methyl-3-{(3-fluorophenyl)sulfonylamino}-2-oxohydropyridyl)acetamide;

N-[3-imino-(1,2,4-oxadiazaperhydrion-6-yl)methyl]-2-(6-methyl-3-{naphthalen-1-ylsulfonylamino}-2-oxohydropyridyl)acetamide;

N-[3-imino-(1,2,4-oxadiazaperhydroin-6-yl)methyl]-2-(6-methyl-3-{naphthalen-2-ylsulfonylamino}-2-oxohydropyridyl)acetamide;

N-[3-imino-(1,2,4-oxadiazaperhydroin-6-yl)methyl]-2-(6-methyl-3-{(2-chlorophenyl)sulfonylamino}-2-oxohydropyridyl)acetamide;

N-[3-imino-(1,2,4-oxadiazaperhydrion-6-yl)methyl]-2-(6-methyl-3-{(4-chlorophenyl)sulfonylamino}-2-oxohydropydidyl)acetamide;

N-[3-imino-(1,2,4-oxadiazaperhydroin-6-yl)methyl]-2-(6-methyl-3-{phenylsulfonylamino}-2-oxohydropyridyl)acetamide;

N-[3-imino-(1,2,4-oxadiazaperhydroin-6-yl)methyl]-2-(6-methyl-3-{naphthalen-1-ylmethylsulfonylamino}-2-oxohydropyridyl)acetamide;

N-[3-imino-(1,2,4-oxadiazaperhydroin-6-yl)methyl]-2-(6-methyl-3-{naphthalen-2-ylmethylsulfonylamino}-2-oxohydropyridyl)acetamide;

N-[3-imino-(1,2,4-oxadiazaperhydroin-6-yl)methyl]-2-(6-methyl-3-{(4-bromophenyl)sulfonylamino}-2-oxohydropyridyl)acetamide;

N-[3-imino-(1,2,4-oxadiazaperhydroin-6-yl)methyl]-2-(6-methyl-3-{(4-fluorophenyl)sulfonylamino}-2-oxohydropyridyl)acetamide;

N-[3-imino-(1,2,4-oxadiazaperhydroin-6-yl)methyl]-2-(6-methyl-3-{(4-iodophenyl)sulfonylamino}-2-oxohydropyridyl)acetamide;

N-[3-imino-(1,2,4-oxadiazaperhydroin-6-yl)methyl]-2-(6-methyl-3-{(4-methoxyphenyl)sulfonylamino}-2-oxohydropyridyl)acetamide;

N-[3-imino-(1,2,4-oxadiazaperhydroin-6-yl)methyl]-2-(6-methyl-3-{(3-trifluoromethylphenyl)sulfonylamino}-2-oxohydropyridyl)acetamide;

N-[3-imino-(1,2,4-oxadiazaperhydrion-6-yl)methyl]-2-(6-methyl-3-{(4-isopropylphenyl)sulfonylamino}-2-oxohydropyridyl)acetamide;

N-[3-imino-(1,2,4-oxadiazaperhydroin-6-yl)methyl]-2-(6-methyl-3-{(3,4-dimethoxyphenyl)sulfonylamino}-2-oxohydropyridyl)acetamide;

N-[3-imino-(1,2,4-oxadiazaperhydroin-6-yl)methyl]-2-(6-methyl-3-{thien-2-ylsulfonylamino}-2-oxohydropyridyl)acetamide;

N-[3-imino-(1,2,4-oxadiazaperhydroin-6-yl)methyl]-2-(6-methyl-3-{(4-vinylphenylsulfonyl)amino}-2-oxohydropyridyl)acetamide;

N-[3-imino-(1,2,4-oxadiazaperhydroin-6-yl)methyl]-2-(6-methyl-3-{(2-butoxy-5-(1,1-dimethylpropyl)phenylsulfonyl)amino}-2-oxohydropyridyl)acetamide;

N-[3-imino-(1,2,4-oxadiazaperhydrion-6-yl)methyl]-2-(6-methyl -3-{(3-nitrophenyl)sulfonylamino}-2-oxohydropyridyl)acetamide;

N-[3-imino-(1,2,4-oxadiazaperhydroin-6-yl)methyl]-2-(6-methyl-3-{(4-methylcarbonylaminophenyl)sulfonylamino}-2-oxohydropyridyl)acetamide;

N-[3-imino-(1,2,4-oxadiazaperhydroin-6-yl)methyl]-2-(6-methyl-3-{(4-tert-butylphenyl)sulfonylamino}-2-oxohydropyridyl)acetamide;

N-[3-imino-(1,2,4-oxadiazaperhydroin-6-yl)methyl]-2-(6-methyl-3-{(3-cyanophenyl)sulfonylamino}-2-oxohydropyridyl)acetamide;

N-[3-imino-(1,2,4-oxadiazaperhydroin-6-yl)methyl]-2-(6-methyl-3-{(4-methylsulfonylphenyl)sulfonylamino}-2-oxohydropyridyl)acetamide;

N-[3-imino-(1,2,4-oxadiazaperhydroin-6-yl)methyl]-2-(6-methyl-3-{dansylamino}-2-oxohydropyridyl)acetamide;

N-[3-imino-(1,2,4-oxadiazaperhydrion-6-yl)methyl]-2-(6-methyl-3-{pentafluorophenyl)sulfonylamino}-2-oxohydropyridyl)acetamide;

N-[3-imino-(1,2,4-oxadiazaperhydroin-6-yl)methyl]-2-(6-methyl-3-{(2-methoxy-5-methylphenyl)sulfonylamino}-2-oxohydropyridyl)acetamide;

N-[3-imino-(1,2,4-oxadiazaperhydroin-6-yl)methyl]-2-(6-methyl-3-{(4-phenylphenyl)sulfonylamino}-2-oxohydropyridyl)acetamide;

N-[3-imino-(1,2,4-oxadiazaperhydrion-6-yl)methyl]-2-(6-methyl-3-{(5-chlorothien-2-yl)sulfonylamino}-2-oxohydropyridyl)acetamide;

N-[3-imino-(1,2,4-oxadiazaperhydroin-6-yl)methyl]-2-(6-methyl-3-{quinolin-8-ylsulfonylamino}-2-oxohydropyridyl)acetamide;

N-[3-imino-(1,2,4-oxadiazaperhydroin-6-yl)methyl]-2-(6-methyl-3-{quinolin-5-ylsulfonylamino}-2-oxohydropyridyl)acetamide;

N-[3-imino-(1,2,4-oxadiazaperhydroin-6-yl)methyl]-2-(6-methyl-3-{1-methylimidazol-4-ylsulfonylamino}-2-oxohydropyridyl)acetamide;

N-[3-imino-(1,2,4-oxadiazaperhydroin-6-yl)methyl]-2-(6-methyl-3-{3-methylquinolin-8-ylsulfonylamino}-2-oxohydropyridyl)acetamide;

N-[3-imino-(1,2,4-oxadiazaperhydroin-6-yl)methyl]-2-(6-methyl-3-{pyridin-2-ylsulfonylamino}-2-oxohydropyridyl)acetamide;

N-[3-imino-(1,2,4-oxadiazaperhydroin-6-yl)methyl]-2-(6-methyl-3-{pyridin-3-ylsulfonylamino}-2-oxohydropyridyl)acetamide;

N-[3-imino-(1,2,4-oxadiazaperhydroin-6-yl)methyl]-2-(6-isopropyl-3-{3-methylphenylsulfonylamino}-2-oxohydropyridyl)acetamide;

N-[3-imino-(1 2,4-oxadiazaperhydroin-6-yl)methyl]-2-(6-ethyl-3-{3-methylphenylsulfonylamino}-2-oxohydropyridyl)acetamide;

N-[3-imino-(1,2,4-oxadiazaperhydroin-6-yl)methyl]-2-(6-propyl -3-{3-methylphenylsulfonylamino}-2-oxohydropyridyl)acetamide;

as well as solvates, hydrates or pharmaceutically acceptable salts (for example, trifluoroacetate and hydrochloride salts) thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula VII may also be solvated, especially hydrated. Hydration may occur during manufacturing of the compounds or compositions comprising the compounds, or the hydration may occur over time due to the hygroscopic nature of the compounds.

Certain compounds within the scope of Formula VII are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$ and/or $R^c$ are $-CO_2R^w$, where $R^w$ is defined above. See, U.S. Pat. No. 5,466,811 and Saulnier et at., Bioorg. Med. Chem. Lett. 4:1985–1990 (1994).

When any variable occurs more than one time in any constituent or in Formula VII, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention includes methods which are useful for in vivo imaging or thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A". Alternatively, the group —A"—L substitutes for the groups —Z—$R^1$ in Formula VII. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, —C(=NH)—(CH$_2$)$_6$—C(=NH)—, —C(=O)—(CH$_2$)$_6$—C(=O)—,

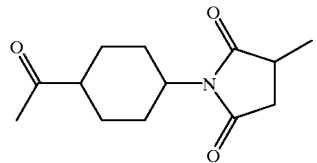

and the like.

Also, in the compounds represented by Formula VII, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., Science 209:295 (1980); Paik C. H. et al., U.S. Pat. No. 4,652,440 (1987); Gries, H. et al., U.S. Pat. No. 4,957,939 (1990). A preferred chelating ligand, L, is 1-(p-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl,1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$ alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl,1,1,3-trimethylbicyclo[2.2.1]heptyl (bornyl), and the like.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5-to 7-membered mono- or bicyclic or stable 7-to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyitolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes I, II, III, and IV outline the synthetic steps to produce compounds of present invention. These schemes illustrate but not limited to the preparation of the compounds of Examples 1 and 2. In addition, a number of intermediates, corresponding to compounds in Schemes 1 and 2, are described in U.S. Pat. No. 6,037,356, issued Mar. 16, 2000. These intermediates are useful for forming compounds of the present invention.

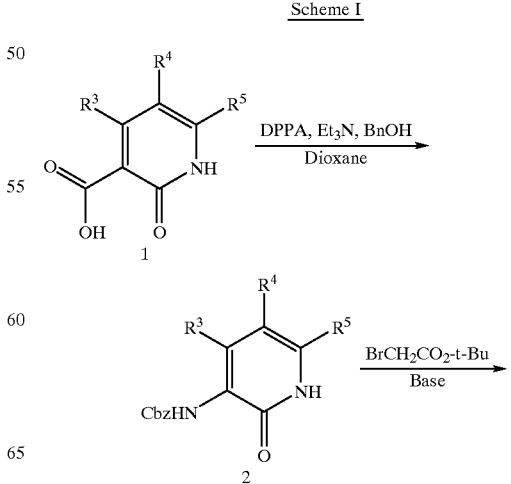

Scheme I

-continued

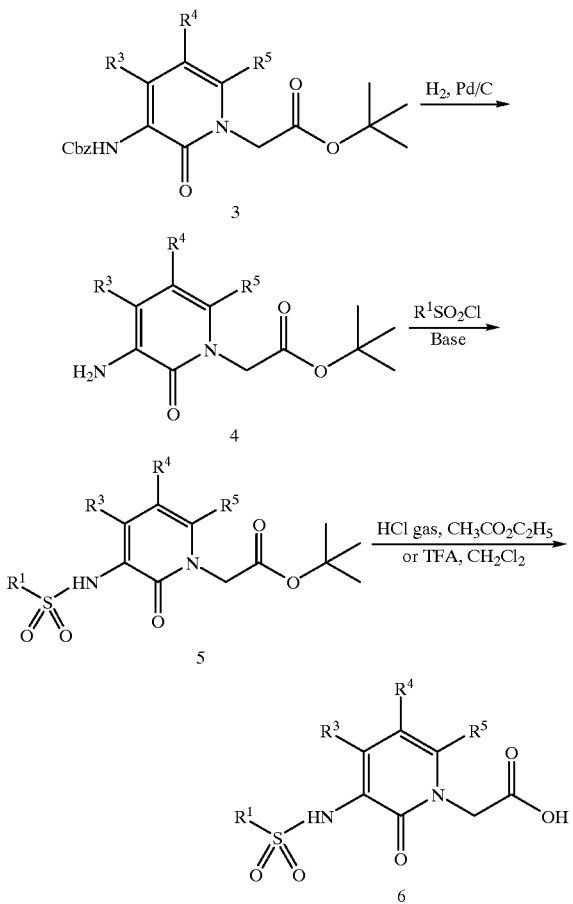

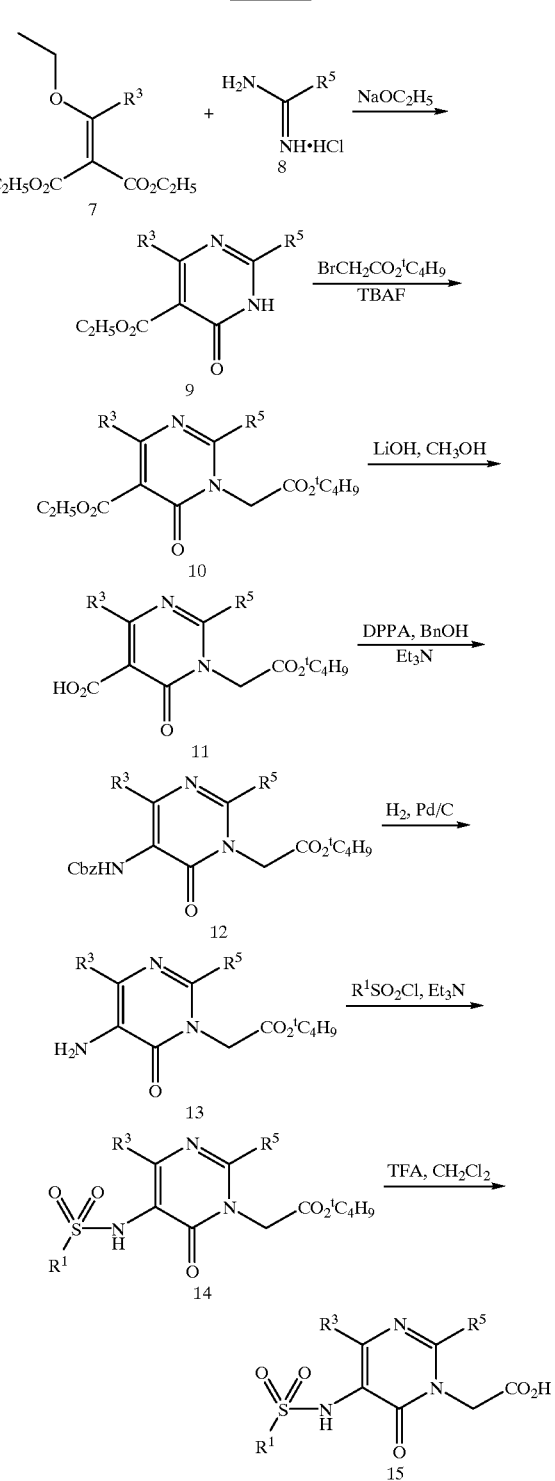

In Scheme I, the 2-hydroxypyridine carboxylic acid 1 is reacted with diphenylphosphoryl azide (DPPA) in the presence of a base, such as triethylamine, to form an acyl azide intermediate which undergoes Curtius rearrangement with benzyl alcohol to form benzyloxycarbonyl (Cbz) protected amino pyridinone 2. This is alkylated with a glycine equivalent, such as tert-butyl bromoacetate, using a base, such as lithium hexamethyldisilazide, cesium carbonate, or sodium hydride, in an appropriate solvent, such as tetrahydrofuran or N,N-dimethylformamide, to give compound 3.

The Cbz group of compound 3 is deprotected using a standard procedure such as hydrogenation in the presence of a catalyst, such as palladium on carbon, in an appropriate solvent, such as tetrahydrofuran and ethanol. The amine 4 is reacted with a sulfonyl chloride in the presence of a base, such as 4-methylmorpholine, in a suitable solvent, such as methylene chloride, to afford 5. The tert-butyl group is removed using a standard procedure well known in art (Greene, T. W., Wuts, P. G. W., *Protecting Groups in Organic Synthesis,* 2nd edition, John Wiley and Sons, Inc. New York, (1991)), such as HCl gas in ethyl acetate or trifluoroacetic acid in methylene chloride, to afford acid 6.

In Scheme II, diethyl ethoxymethylenemalonate 7 is treated with amidine 8 in the presence of a base, such as sodium ethoxide, in ethanol to afford substituted pyrimidine 9. This is alkylated with a glycine equivalent, such as tert-butyl bromoacetate, using a base, such as tetrabutylammonium fluoride, lithium hexamethyldisilazide, or sodium hydride, in an appropriate solvent, such as tetrahydrofuran or N,N-dimethylformamide to give ester 10. The ethyl ester is selectively hydrolyzed with lithium hydroxide in a suitable solvent, such as methanol or ethanol, to afford acid 11.

The acid 11 is then treated with diphenylphiosphoryl azide (DPPA) in the presence of a base, such as triethylamine, to form an acyl azide intermediate which undergoes Curtius rearrangement with benzyl alcohol to form benzyloxycarbonyl (Cbz) protected 5-aminopyrimidione 12. The Cbz group of compound 12 is deprotected using a standard procedure, such as hydrogenation in the presence of a catalyst, such as palladium on carbon, in an appropriate solvent, such as tetrahydrofuran and ethanol. The amine 13 is then treated with a sulfonyl chloride in the presence of a base, such as 4-methylmorpholine or triethylamine, in a suitable solvent, such as methylene chloride, to afford 14. The tert-butyl group is removed using a standard procedure well known in art (Greene, T. W., Wuts, P. G. W., *Protecting Groups in Organic Synthesis,* 2nd edition, John Wiley and Sons, Inc. New York, (1991)), such as tulfluoroacetic acid in methylene chloride, to afford acid 15.

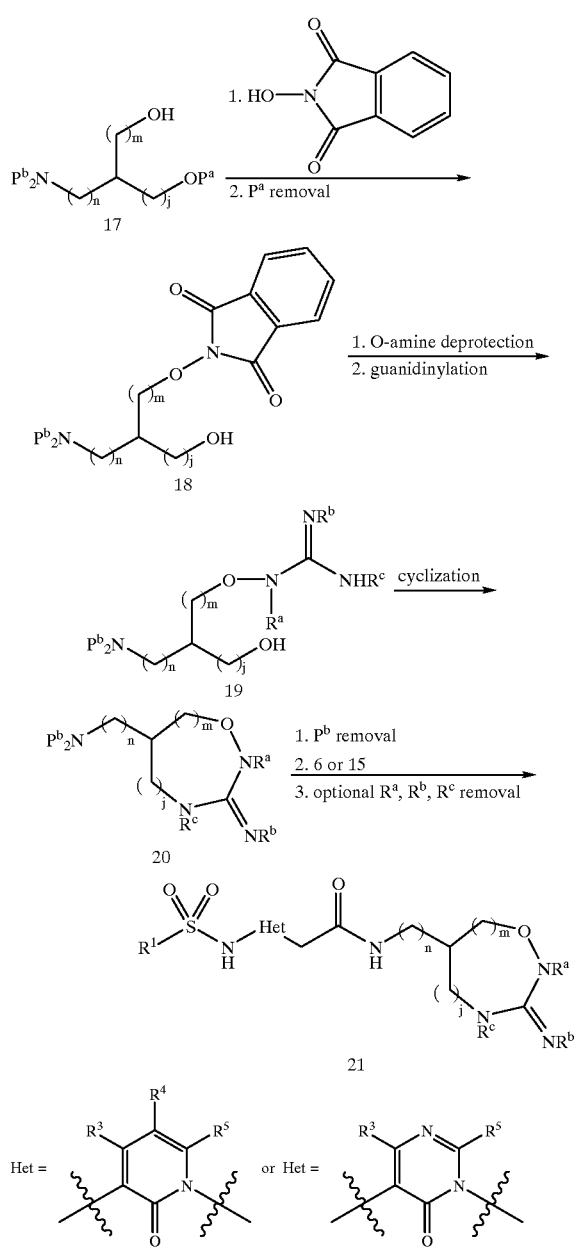

In Scheme III, alcohols 17 are reacted with N-hydroxyphthalimide under Mitsunobu conditions. Preferred conditions include using a triarylphosphine, such as triphenylphosphine, and an azodicarbonyl reagent, such as diethyl azodicarboxylate, in a suitable solvent, such as tetrahydrofuran. Removal of the hydroxyl protecting groups to give compounds 18 is accomplished by using standard reaction conditions. Preferred conditions for deprotection of 4-methoxyphenyl ethers involve using ammonium cerium nitrate in a mixture solvents of acetonitrile and water.

Unblocking of the phthalimide protecting group is accomplished by employing methylamine in a suitable solvent, such as ethanol. Guanidinylation of the resulting alkoxyamines may be achieved employing a variety of guanidinylating reagents available such as N,N'-bis(tert-butoxycarbonyl)-1H-pyrazole-1-carboxamidine. Intramolecular cyclization of 19 occurs to provide compounds 20 under standard Mitsunobu conditions. Deprotection of the primary amine protecting groups is routinely accomplished using the conventional reaction conditions. For example, benzyloxycarbonyl protecting group may be removed through catalytic hydrogenation using palladium on carbon as a catalyst in a solvent such as methanol or tetrahydrofuran.

The resulting amine compounds are coupled with acid 6 or 15 in the presence of diisopropylethyl amine and a suitable coupling reagent, such as Castro's reagent (BOP), in a polar solvent, such as N,N-dimethylformamide. When $R^a$, $R^b$, and $R^c$ are protecting groups, for example tert-butyloxycarbonyl (Boc), these protecting groups can be optionally removed by treatment with an acid, usully trifluoroacetic acid, in a suitable solvent, such as dichloromethane.

In Scheme IV, aminolactones 22 are protected as benzylcarbamates under standard reaction conditions. Aminolysis of the protected aminolactones effects in the presence of an amine, such as N,O-dimethylhydroxyamine, and a Lewis acid, such as aluminum chloride or trimethylaluminum, in a suitable solvent such as dichloromethane or 1,2-dichloroethane. The resulting N-methoxy-N-methyl amides may be protected as a variety of ethers, for example tetrahydropyranyl ethers, under standard conditions.

Under standard conditions amides 23 are converted to alcohols 24 stepwise. The sequence may include three steps: (1) hydrolysis of the amides 23 to carboxylic acids in a basic alcoholic aqueous solution, (2) esterification of the acids to alkyl carboxylic esters, and (3) reduction of the esters using an appropriate reducing agent such as lithium borohydride. Alternatively, the amides 23 may be reduced to alcohols 24 in two steps employing suitable reducing agents. For example, Weinreb amides 23 ($R^d$=Me; $R^e$=OMe) may be reduced with lithium aluminum hydride under carefully controlled conditions to aldehydes, which are subsequently reduced to alcohols 24.

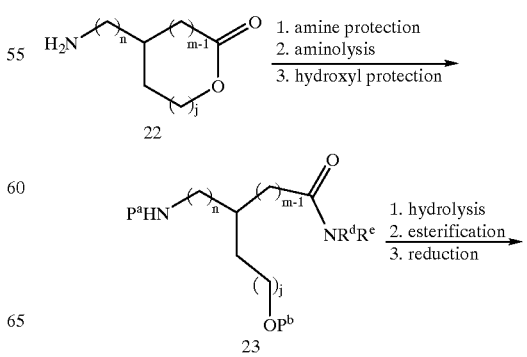

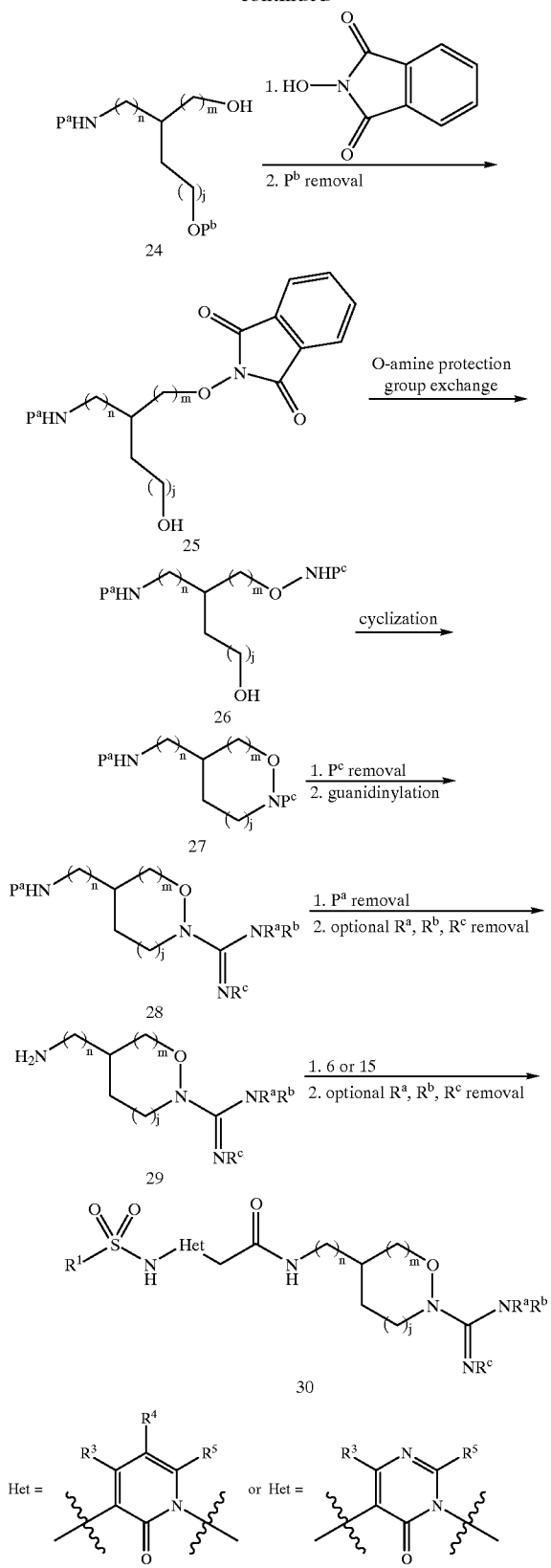

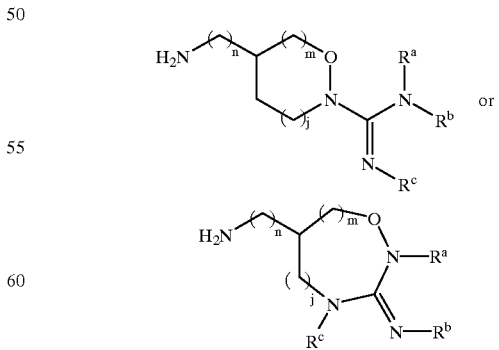

Under standard Mitsunobu conditions alcohols 24 are reacted with N-hydroxyphthalimide. Removal of hydroxy protecting groups to give compounds 25 is accomplished by using standard conditions. For example, tetrahydropyranyl ethers may be removed by treatment with acids, such as acetic acid, in a suitable aqueous solution, such as water and tetrahydrofuran. Exchanging of O-amine protecting groups to secondary O-amines 26 is achieved by treatment of the phthalimides 25 with methylamine follow by protection of the released amines to carbamates 26, such as tert-butoxycarbamates, in biphasic system composed of an organic solvent, such as dichloromethane, and a basic aqueous phase.

Under standard Mitsunobu conditions intramolecular cyclization of 26 occurs to give cyclic compounds 27. Preferred conditions include using a triarylphosphine, such as triphenylphosphine, and an azodicarbonyl reagent, such as diethyl azodicarboxylate, in a suitable solvent, such as tetrahydrofuran. Deprotection of the amino protecting groups is routinely accomplished using the conventional conditions. For example, tert-butyloxycarbonyl (Boc) may be removed in acidic solutions, such as trifluoroacetic acid in dichloromethane. Guanidinylation of the resulting cyclic O-amines may be achieved employing a variety of guanidinylating reagents available such as N,N'-bis(tert-butoxycarbonyl)-1H-pyrazole-1-carboxamidine.

Deprotection of the primary amine blocking groups in 28 is routinely accomplished using conventional reaction conditions. For example, benzyloxycarbonyl protecting group may be removed through catalytic hydrogenation using palladium on carbon as a catalyst in a solvent such as methanol or tetrahydrofuran. Alternatively, when $R^a$, $R^b$, and $R^c$ are protecting groups, for example tert-butyloxycarbonyl, these protecting groups can be optionally removed at the same time with the $P^a$ protecting group, when $P^a$ is benzyloxycarbonyl group. Strong acids such as hydrobromic acid in acetic acid may be used to effect this operation.

Amines 29 are coupled with acid 6 or 15 in the presence of diisopropylethyl amine and a suitable coupling reagent, such as Castro's reagent (BOP), in a polar solvent, such as N,N-dimethylformamide. When $R^a$, $R^b$, and $R^c$ are protecting groups, for example tert-butyloxycarbonyl, these protecting groups can be optionally removed by treatment with an acid, usully trifluoroacetic acid, in a suitable solvent such as dichloromethane.

Thus, the invention also relates to a process for preparing a cyclic oxyguanidine compound of the invention, comprising:

coupling or condensing a compound of formula:

or a salt thereof, where $R^a$, $R^b$ and $R^c$ are as defined herein or optionally protected, and n, m and j are as defined herein, with a compound of Formula XI:

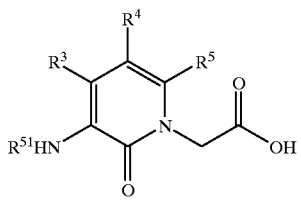

where $R^{51}$ is H or $R^1$-X-, where $R^1$, X, $R^3$, $R^4$, $R^5$, $R^a$, $R^b$, and $R^c$ are as defined herein. In general, protecting groups for the $R^a$, $R^b$, and $R^c$ groups may be employed where any one of $R^a$, $R^b$, and $R^c$ are hydrogen.

The pharmaceutically-acceptable salts of the compounds of Formula VII (in the form of water- or oil-soluble or dispersible products) include the conventional non-toxic salts or the quaternary ammonium salts which are formed, e.g., from inorganic or organic acids or bases. Examples of such acid addition salts include acetate, adipate, alinate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrlidone, polyhydroxypropylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula VII is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4°C. A protein fraction precipitates during dialysis and is isolated by centrifugation. This fraction contains most of the chymotrypsin-like activity of leukocyte granules. Specific substrates are prepared for each enzyme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25°C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula VII can be labeled with radioactive iodine by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula VII complexed with a radioactive atom.

For the compounds of Formula VII, suitable radioactive atoms include Co-57, Cu-67, Ga-67, Ga-68, Ru-97, Tc-99m, In-111, In-113m, Hg-197, Au-198, and Pb-203. In particular, technetium-99m (Tc-99m) is an ideal radioactive atom for imaging because of its nuclear properties. It is a gamma emitter and has a single photon energy of 140 keV, a half-life of about 6 hours, and it is readily available from a Mo-99/Tc-99 generator. Rhenium-186 and -188 also have gamma emission which allows them to be imaged. Preferred compositions contain the radioactive atom, Tc-99m.

Compositions of the present invention are conveniently prepared by completing a compound of Formula VII with radioisotopes which are suitable for detection externally.

The compounds of Formula VII can be labeled by any of the many techniques known in the art to provide a composition of the present invention. For example, these compounds can be labeled through a chelating agent such as diethylene-triaminepentaacetic acid (DTPA) or metallothionein, both of which can be covalently attached to the compound of Formula VII.

In general, the compositions of the present invention containing technetium-99m are prepared by forming an aqueous mixture of technetium-99m and a reducing agent and a water-soluble ligand, and then contacting the mixture with a compound of the present invention represented by Formula VII. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula VII having a DTPA chelating means with technetium-99m. This may be accomplished by combining a predetermined amount (as 5 $\mu$g to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula VII having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula VII having a metallothionein attached thereto. After incubating the mixture for a period of time and under conditions which allow for an exchange of the technetium-99m from the glucoheptonate complex to the metallothionein of the compound of Formula VII, the technetium-labeled composition of the present invention is formed.

The source of technetium-99m should preferably be water soluble. Preferred sources are alkali and alkaline earth metal pertechnetate ($TcO_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. For example, stannous chloride ($SnCl_2$) is the reducing agent and can be used in range from 1–1,000 µg/mL. Especially preferred concentrations are about 30–500 µg/mL.

Citric acid complexes with technetium-99m to quickly form a stable technetium-99m-citrate complex. Upon contact with a compound of Formula VII, substantially quantitative transfer of technetium-99m from its citrate complex to the chelating means of the compound of Formula VII is achieved rapidly and under mild conditions. The amount of citric acid (as sodium citrate) can range from about 0.5 mg/ml up to the amount maximally soluble in the medium. Preferred amounts of citric acid range from 15 to 30 µg/ml.

The amount of compound of Formula VII having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

Alternative compositions of the present invention include an In-111 labeled compound of the present invention.

The present invention also includes compositions of the compounds of the present invention which are useful for in vivo imaging of thrombi in a mammal, comprised of a compound represented by Formula VII complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysoprosium (III), holmium(III), and erbium(III) are preferred. Especially preferred for the paramagnetic atom is gadolinium(III).

The compositions of the present invention may be prepared by combining a compound of Formula VII with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula VII in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of a radiolabeled compound of Formula VII. Compositions such as those described above may be conveniently used in these diagnostic compositions.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 µCi, preferably about 10 µCi. Magnetic resonance imaging will require that the dose provided be about 0.001 to 5 mmole/kg, preferably about 0.005 to 0.5 mmole/kg of a compound of Formula VII complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences,* Mack Publishing Co. (A. R. Gennaro edit. 1985).

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. At 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula VII having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

N-[(3-Imino(1,2,4-oxadiazaperhydroin-6-yl)) methyl]-2-(6methyl-3-{[(3methylphenyl)sulfonyl] amino}-2-oxohydropyridyl)acetamide trifluoroacetate

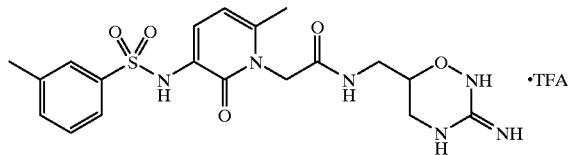

1. N-(6-Methyl-2-oxo(3-hydropyridyl)) (phenylmethoxy)carboxamide

Diphenylphosphoryl azide (11.9 mL, 55 mmol) was added to a solution of 2-hydroxy-6-methylpyridine-3-carboxylic acid (7.65 g, 50 mmol) and triethylamine (7.7 mL, 55 mmol) in dry dioxane (100 mL) and the resulting solution was heated to reflux. After 16 h more triethylamine (7.7 mL, 55 mmol) and benzyl alcohol (5.7 mL, 50 mmol) were added and the solution was refluxed for another 24 h. The reaction mixture was concentrated in vacuo, and the residue was partitioned between methylene chloride (200 mL) and brine (100 mL) after acidified to pH 1 with 10% HCl. The organic layer was washed with saturated $NaHCO_3$ (2×100 mL) and brine (100 mL), dried over $Na_2SO_4$ and filtered. After evaporating the solvent in vacuo, methanol (100 mL) and hexane (20 mL) were added to the residue. The solid was collected, washed with methanol (50 mL), and dried to give the title compound as a white solid (7.2 g, 56%). $^1$H NMR ($CDCl_3$) δ12.82 (s, 1 H), 8.06 (d, 1 H, J=7.0 Hz), 7.69 (s, 1 H), 7.42 (m, 5 H), 6.09 (d, 1H, J=7.5 Hz), 5.22 (s, 2 H), 2.32 (s, 3 H).

2. tert-Butyl 2-{6-methyl-2-oxo-3-[(phenylmethoxy) carbonylamino]hydropyridyl}acetate tert-Butyl bromoacetate (3.9 g, 20 mmol) was added to a stirred suspension of the product (5.15 g, 20 mmol) of the preceding step and $Cs_2CO_3$ (6.5 g, 20 mmol) in N,N-dimethylformamide (50 mL). After stirring at 40° C. overnight, the solid was removed by filtration and the filtrate was concentrated under high vacuum. The residue was dissolved in ethyl acetate (150 mL), washed with water (2×50 mL) and brine (50 mL), dried over $Na_2SO_4$, and concentrated in vacuo. The residue was purified by flash chromatography (25% ethyl acetate in hexane) to give the title compound as a white crystalline solid (4.2 g, 56%). $^1$H NMR ($CDCl_3$) δ7.95 (d, 1 H, J=7.3 Hz), 7.76 (s, 1 H), 7.37 (m, 5 H), 6.09 (d, 1 H, J=7.6 Hz), 5.19 (s, 2 H), 4.75 (s, 2 H), 2.32 (s, 3 H), 1.47 (s, 9 H).

3. tert-Butyl 2-(3-amino-6-methyl-2-oxohydropyridyl)acetate

A mixture of the product (4.1 g, 11 mmol) of the preceding step and 10% Pd/C (400 mg) in ethanol (100 mL) was hydrogenated under hydrogen (balloon) for 1.5 h. The catalyst was removed by filtration through Celite and the filtrate was concentrated to give the title compound as a white solid (2.55 g, 97%). $^1$H NMR ($CDCl_3$) δ6.49 (d, 1 H, J=7.3 Hz), 5.92 (d, 1 H, J=7.3 Hz), 4.75 (s, 2 H), 2.19 (s, 3 H), 1.47 (s, 9 H).

4. tert-Butyl 2-(6-methyl-3-{[(3-methylphenyl) sulfonyl]amino}-2-oxohydropyridyl)acetate To a solution of tert-butyl 2-(3-amino-6-methyl-2-oxohydropyridyl)acetate (1.42 g, 5.88 mmol), as prepared in the preceding step, and N-methylmorpholine (1.29 mL, 11.76 mmol) in methylene chloride (40 mL) was added 3-methylbenzenesulfonyl chloride (1.12 g, 5.88 mmol) at 0° C. After stirring at room temperature overnight, the reaction mixture was diluted with methylene chloride (60 mL), washed with saturated $NaHCO_3$ (2×50 mL), 10% citric acid (3×50 mL) and brine (50 mL), and dried over $Na_2SO_4$. After evaporating the solvent, the residue was purified by flash chromatography (5 to 10% ethyl acetate in methylene chloride) to give the title compound as a white solid (2.1 g, 91%). $^1$H NMR ($CDCl_3$) δ7.63 (m, 2 H), 7.55 (s(b), 1 H), 7.42 (d, 1 H, J=8 Hz), 7.32 (m, 2 H), 6.01 (d, 1 H, J=8 Hz), 4.64 (s, 2 H), 2.37 (s, 3 H), 2.20 (s, 3 H), 1.43 (s, 9 H).

5. 2-(6-Methyl-3-{[(3-methylphenyl)sulfonyl] amino}-2-oxohydro pyridyl)acetic acid HCl gas was bubbled through a stirred suspension of the product (2.0 g, 5.09 mmol) of the preceding step in ethyl acetate (50 mL) at 0° C. until a solution was formed. After warming to room temperature over 2 h, a thick suspension was formed. The mixture was degassed with nitrogen and filtered to give the title compound as a white solid (1.36 g, 80%). $^1$H NMR (DMSO-d6) δ9.38 (s, 1 H), 7.62 (m, 2 H), 7.41 (m, 2 H), 7.25 (d, 1 H, J=8 Hz), 6.09 (d, 1 H, J=8 Hz), 4.67 (s, 2 H), 2.35 (s, 3 H), 2.20 (s, 3 H).

6. 1-[Bisbenzylamino]-3-(4-methoxyphenoxy)propan-2-ol

A solution of glycidyl 4-methoxyphenyl ether (1.10 g, 6.10 mmol), dibenzylamine (1.25 g, 6.33 mmol), and anhydrous ethyl alcohol (20 mL) was heated at 80° C. for 2 days. The solvent was evaporated under reduced pressure to give the title compound as a clear oil (2.36 g, 100%). $^1$H NMR (CDCl$_3$) δ7.35–7.30 (m, 7 H), 7.28–7.25 (m, 3 H), 6.82–6.76 (m, 4 H), 4.10–4.07 (m 1 H), 3.83–3.81 (m, 3 H), 3.78–3.76 (m, 1 H), 3.76 (s, 3 H), 3.53 (d, 2 H, J=13.4 Hz), 2.66 (d, 2 H, J=6.5 Hz). Mass spectrum (LCMS, ESI) calcd. for C$_{24}$H$_{27}$NO$_3$: 378 (M+H). Found: 378.

7. N-[2-Hydroxy-3-(4-methoxyphenoxy)propyl](phenylmethoxy)carboxamide

A mixture of 1-[bisbenzylamino]-3-(4-methoxyphenoxy)propan-2-ol (1.26 g, 3.74 mmol), as prepared in the preceding step, 10% palladium on carbon (125 mg) and methanol (120 mL) was degassed under reduced pressure and refilled with H$_2$ gas several times. After stirring under 1 atm H$_2$ balloon at room temperature overnight, the mixture was filtered through Celite and washed with methanol. The filtrate was concentrated to a white solid (0.78 g, 100%). This solid (0.78 g, 3.96 mmol) was dissolved in methanol (20 mL), dichloromethane (20 mL), and water (10 mL). To this solution were added sodium bicarbonate (0.83 g, 9.88 mmol) and benzyl chloroformate (0.7 mL, 4.66 mmol) at room temperature. After stirring for 4 hours, the solution was concentrated and the residue was partitioned between dichloromethane and water. The organic layer was dried (Na$_2$SO$_4$), concentrated, and flash chromatographed on silica gel to give the title compound as a white solid (1.00 g, 80.8%). $^1$H NMR (CDCl$_3$) δ7.37–7.33 (m, 5 H), 6.83 (s, 4 H), 5.20 (m, 1 H), 5.12 (s, 2 H), 4.10 (m, 1 H), 3.94–3.88 (m, 2 H), 3.77 (s, 3 H), 3.53–3.47 (m, 1 H), 3.38–3.27 (m, 1 H), 2.95 (m, 1 H).

8. N-[2-(1,3-Dioxoisoindolin-2-yloxy)-3-(4-methoxyphenoxy)propyl](phenylmethoxy)carboxamide To a solution of the product (1.00 g, 3.02 mmol) of the preceding step, triphenylphosphine (1.03 g, 3.93 mmol), N-hydroxyphthalimide (0.54 g, 3.31 mmol), and tetrahydrofuran (100 mL) was added diethyl azodicarboxylate (0.62 mL, 3.94 mmol) at 4° C. After stirring at 4° C. to room temperature overnight, the solution was concentrated in vacuo and flash chromatographed (SiO$_2$) to provide the title compound, which contaminated with 1,2-dicarbethoxyhydrazine, as a yellow semi-solid (1.79 g). $^1$H NMR (CDCl$_3$) δ7.85 (m, 2 H), 7.78 (m, 2 H), 7.41–7.31 (m, 5 H), 6.82–6.78 (m, 4 H), 6.07 (m, 1 H), 5.16 (d, 2 H, J=3.2 Hz), 4.53 (m, 1 H), 4.28–4.25 (m, 2 H), 3.76 (s, 3 H), 3.74–3.66 (m, 2 H).

9. N-[2-(1,3-Dioxoisoindolin-2-yloxy)-3-hydroxypropyl](phenylmethoxy)carboxamide To a solution of the product (53 mg, 0.10 mmol) of the preceding step in acetonitrile (4 mL) and water (1 mL) at 4° C. was added ammonium cerium nitrate (150 mg, 0.274 mmol). After 15 min at 4° C., ethyl acetate and brine were added. The organic layer was separated and the aqueous layer was extracted with ethyl acetate. The combined organic layers were washed with saturated sodium hydrogensulfite and sodium bicarbonate. Drying (Na$_2$SO$_4$), concentration, and flash chromatography produced the title compound as a yellow oil (40 mg, 96.7%). $^1$H NMR (CDCl$_3$) δ7.88–7.85 (m, 2 H), 7.82–7.78 (m, 2 H), 7.41–7.30 (m, 5 H), 6.08 (m, 1 H), 5.16 (s, 2 H), 4.28–4.24 (m, 1 H), 3.78–3.72 (m, 3 H), 3.59–3.46 (m, 2H).

10. tert-Butyl-2-aza-3-[(tert-butoxy)carbonylamino]-3-[(2-hydroxy-1-{[(phenylmethoxy)carbonylamino]methyl}ethoxy)amino]prop-2-enoate The product (650 mg, 1.76 mmol) of the preceding step in methanol (15 mL) was treated with 40 wt. % methylamine in water (680 mg, 8.77 mmol) for 2 h at room temperature. After removal of the solvents under reduced pressure, the remaining brown solid was dissolved in anhydrous N,N-dimethylformamide (20 mL) and reacted with N,N'-bis(tert-butoxycarbonyl)-1H-pyrazole-1-carboxamidine (1.09 g, 3.52 mmol) at 50° C. overnight. The solution was concentrated and flash chromatographed (SiO$_2$) to provide the title compound as an orange oil (776 mg, 91.6%, 2 steps). $^1$H NMR (CDCl$_3$) δ9.12 (s, 1 H), 7.67 (s, 1 H), 7.36–7.33(m, 5 H), 5.60 (m, 1 H), 5.12 (s, 2 H), 4.19 (m, 1 H), 3.87–3.76 (m, 2 H), 3.56 (t, 2 H, J=5.9 Hz), 1.50 (s, 9 H), 1.46 (s, 9 H).

11. tert-Butyl 2-aza-2-(4-[(tert-butyl)oxycarbonyl]-6-{[(phenylmethoxy)carbonylamino]methyl}(1,2,4-oxadiazaperhydroin-3-ylidene))acetate To a solution of the product (770 mg, 1.60 mmol), as prepared in the preceding step, triphenylphosphine (840 mg, 3.21 mmol), and tetrahydrofuran (50 mL) was added diethyl azodicarboxylate (0.500 mL, 3.18 mmol) at 4° C. After at 4° C. for 20 min, the cooling bath was removed and the solution was stirred at room temperature for 3 h. Concentration and flash chromatography yielded the title compound as a yellow oil (702 mg, 94.7%). $^1$H NMR (CDCl$_3$) δ8.10 (s, 1 H), 7.35 (s, 5 H), 5.33 (t, 1 H, J=5.8 Hz), 5.10 (s, 2 H), 3.99–3.91 (m, 2 H), 3.62–3.57 (m, 1 H), 3.44 (dd, 1 H, J=9.4, 12.0 Hz), 3.32–3.27 (m, 1 H), 1.51 (s, 9 H), 1.47 (s, 9 H). Mass spectrum (LCMS, ESI) calcd. for C$_{22}$H$_{32}$N$_4$O$_7$: 487 (M+Na). Found: 487.

12. tert-Butyl 2-{6-(aminomethyl)-4-[(tert-butyl)oxycarbonyl](1,2,4-oxadiazaperhydroin-3-ylidene)}-2-azaacetate The mixture of the product (702 mg, 1.51 mmol) of the preceding step, 10% palladium on carbon (80 mg), and methanol (30 mL) was degassed under reduced pressure and refilled with H$_2$ gas several times. The mixture was stirred under 1 atm H$_2$ balloon at room temperature for 5 h. After concentration and flash chromatography on silica gel, the title compound was obtained as white foam (205 mg, 41.1%). $^1$H NMR (CDCl$_3$) δ5.55 (s, 1 H), 3.92–3.88 (m, 1 H), 3.59–3.44 (m, 3 H), 3.05–2.91 (m, 1 H), 1.51 (s, 9 H), 1.47 (s, 9 H).

13. tert-Butyl 2-aza-2-(4-[(tert-butyl)oxycarbonyl]-6-{[2-(6-methyl-3-{[(3-methylphenyl)sulfonyl]amino}-2-oxohydropyridyl)acetylamino]methyl}(1,2,4-oxadiazaperhydroin-3-ylidene))acetate To a solution of the product of the preceding step (200 mg, 0.606 mmol) and 2-(6-methyl-3-{[(3-methylphenyl)

sulfonyl]amino}-2-oxohydropyridyl)acetic acid (210 mg, 0.625 mmol), as prepared in Example 1, step 5, in N,N-dimethylformamide (5 mL) was added N,N-diisopropylethylamine (240 mg, 1.86 mmol) and Castro's reagent (302 mg, 0.682 mmol). After stirred at room temperature overnight, the reaction solution was concentrated and the residue was partitioned between dichloromethane and 10% citric acid (×2). The combined organic phases were dried (Na$_2$SO$_4$), concentrated, and flash chromatographed (SiO$_2$) to provide the title compound as white foam (289 mg, 73.6%). $^1$H NMR (CDCl$_3$) δ9.48 (s, 1 H), 8.12 (s, 1 H), 7.63–7.60 (m, 2 H), 7.32–7.27 (m, 3 H), 6.01 (d, 1 H, J=7.7 Hz), 4.80 (d, 1 H, J=15.5 Hz), 4.70 (d, 1 H, J=15.7 Hz), 4.03 (m, 1 H), 3.89 (dd, 1 H, J=2.9, 12.2 Hz), 3.53–3.41 (m, 3 H), 2.33 (s, 3 H), 2.29 (s, 3H), 1.53 (s, 9 H), 1.43 (s, 9 H). Mass spectrum (LCMS, ESI) calcd. for C$_{29}$H$_{40}$N$_6$O$_9$S: 671 (M+Na), 649 (M+H). Found: 671, 649.

14. N-[(3-Imino(1,2,4-oxadiazaperhydroin-6-yl)) methyl]-2-(6-methyl-3-{[(3-methylphenyl)sulfonyl] amino}-2-oxohydropyridyl)acetamide trifluoroacetate A solution of the product of the preceding step (260 mg, 0.401 mmol) in trifluoroacetic acid (3 mL) and dichloromethane (6 mL) was stirred at room temperature for 2 h. The solution was concentrated in vacuo and purified on Water's sep-pak (SiO$_2$, 10 g) to give the title compound as a white solid (150 mg, 83.4%). $^1$H NMR (DMSO-d$_6$) δ11.52 (s, 1 H), 9.27 (s, 1 H), 8.66 (s, 1 H), 8.55 (t, 1 H, J=5.7 Hz), 7.67 (s, 1 H), 7.64–7.61 (m, 1 H), 7.45–7.39 (m, 3 H), 7.23 (d, 1 H, J=7.6 Hz), 6.07 (d, 1 H, J=7.6 Hz), 4.62 (s, 2 H), 3.96–3.94 (m, 1 H), 3.39–3.29 (m, 2 H), 3.17–3.10 (m, 2 H), 2.35 (s, 3 H), 2.18 (s, 3 H). Mass spectrum (LCMS, ESI) calcd. for C$_{19}$H$_{24}$N$_6$O$_5$S: 471 (M+Na), 449 (M+H). Found: 471, 449.

EXAMPLE 2

5-[2-(6-Methyl-3-{[(3-methylphenyl)sulfonyl] amino}-2-oxohydropyridyl)acetylamino]-1,2-oxazaperhydroine-2-carboxamidine trifluoroacetate

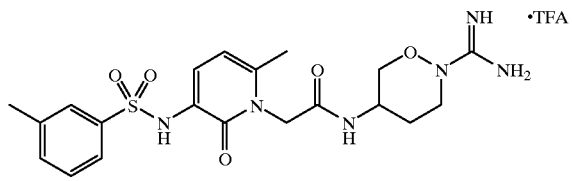

1. N-(2-Oxo(3-3,4,5-trihydrofuryl))(phenylmethoxy)carboxamide

To a rapidly stirred mixture of α-amino-γ-butyrolactone hydrobromide (6.06 g, 33.3 mmol), sodium bicarbonate (14.0 g, 167 mmol), dichloromethane (50 mL), and water (50 mL) was added a solution of benzyl chloroformate (7.0 mL, 46.6 mmol) in dichloromethane (20 mL) dropwise via an addition funnel at room temperature. The solution was stirred overnight and then filtered. The filtrate was separated and the aqueous layer was extracted with dichloromethane. The combined organic layers were dried (Na$_2$SO$_4$), concentrated, and flash chromatographed to provide the title compound as a white solid (7.33 g, 93.7%). $^1$H NMR (CDCl$_3$) δ7.41–7.31 (m, 5 H), 5.32 (s(b), 1 H), 5.14 (s, 2 H), 4.49–4.37 (m, 2 H) 4.30–4.22 (m, 1 H), 2.84–2.76 (m, 1 H), 2.29–2.14 (m, 1 H).

2. 4-Hydroxy-N-methoxy-N-methyl-2-[(phenylmethoxy)carbonylamino]butanamide

To a suspension of aluminum chloride (4.30 g, 32.3 mmol) in anhydrous dichloromethane (200 mL) at 4° C. was added triethylamine (6.52 g, 64.6 mmol) in about 10 minutes. After completion of the addition, the cooling bath was removed and the homogeneous solution was stirred for 15 min. The product (5.06 g, 21.5 mmol) of the preceding step and N,O-dimethyl hydroxyamine hydrochloride (2.52 g, 25.8 mmol) were added at room temperature. After stirring for 5 h, the reaction was quenched with water dropwise at 4° C. and stirring was continued for about 0.5 h. The mixture was filtered, the filtrate was separated, and the aqueous layer was extracted with dichloromethane. The combined organic phases were washed with water, dried (Na$_2$SO$_4$), concentrated, and flash chromatographed to give the title compound as a clear oil (5.93 g,93.0%). $^1$H NMR (CDCl$_3$) δ7.37–7.32 (m, 5 H), 5.83 (d, 1 H, J=8.0 Hz), 5.12 (d, 2 H, J=4.3 Hz), 4.87 (m, 1 H), 3.78 (s, 3 H), 3.73–3.65 (m, 2 H), 3.22 (s, 3 H), 3.11 (t, 1 H, J=6.6 Hz), 2.10–2.05 (m, 1 H), 1.65–1.55 (m, 1 H).

3. N-methoxy-N-methyl-4-perhydro-2H-pyran-2-yloxy-2-[(phenylmethoxy)carbonylamino] butanamide A solution of the product (2.43 g, 8.21 mmol) of the preceding step, 3,4-dihydro-2H-pyran (2.07 g, 24.6 mmol), and pyridinium p-toluenesulfonate (200 mg, 0.796 mmol) in dichloromethane (50 mL) was stirred at room temperature overnight. Water was added and the aqueous layer was extracted with dichloromethane. The combined organic phases were dried (Na$_2$SO$_4$) and concentrated to give the title compound as a yellow oil (3.00 g, 96.2%). $^1$H NMR (CDCl$_3$) δ7.37–7.30 (m, 5 H), 5.76 (t, 1 H, J=8.1 Hz), 5.16–5.03 (m, 2 H), 4.85–4.81 (m, 1 H), 4.58 (s, 1 H), 3.89–3.81 (m, 1 H), 3.79 (s, 3 H), 3.51–3.40 (m, 2 H), 3.22 (s, 3 H), 2.25–1.50 (m, 9 H).

4. N-[2-Hydroxy-1-(2-perhydro-2H-pyran-2-yloxyethyl)ethyl](phenylmethoxy)carboxamide The product (2.86 g, 7.53 mmol) of the preceding step in ethyl alcohol (60 mL) and water (15 mL) was treated with potassium hydroxide (1.69 g,30.2 mmol) at room temperature overnight. After removal of ethyl alcohol under reduced pressure, the residue was diluted with dichloromethane and acidified to pH~3 with 10% hydrochloric acid. The organic layer was separated and the aqueous layer was extracted with dichloromethane. A yellow oil (2.36 g, 93.0%) was obtained after drying and removal of dichloromethane in vacuo. To this oil (2.36 g, 7.00 mmol) in acetone (100 mL) was added potassium carbonate (1.94 g, 14.1 mmol) and iodomethane (1.30 mL, 20.9 mmol). The reaction mixture was heated at 60° C. overnight and filtered. The filtrate was concentrated and the residue was partitioned between dichloromethane and water. Drying and evaporation of solvent produced a yellow oil (2.30 g, 93.6%), which was diluted with tetrahydrofuran (30 mL) and treated with 2.0 M lithium borohydride (4.0 mL, 8.0 mmol) for 2.5 h at room temperature. The reaction was quenched with a few drops of water. Brine and dichloromethane work-up, drying and removal of solvents yielded the title compound as a yellow oil (2.00 g, 94.5%). $^1$H NMR (CDCl$_3$) δ7.38–7.29 (m, 5 H), 5.47 (m, 1 H), 5.10 (s, 2 H), 4.59–4.52 (m, 1 H), 3.92–3.65 (m, 5 H), 3.53–3.46 (m, 2 H), 2.99–2.94 (m, 1 H), 1.98–1.49 (m, 8 H).

5. N-{1-[(1,3-Dioxoisoindolin-2-yloxy)methyl]-3-perhydro-2H-pyran-2-yloxypropyl}(phenylmethoxy)carboxamide To a solution of the product (2.00 g, 6.19 mmol), as prepared in the preceding step, triphenylphosphine (2.23 g, 8.51 mmol), N-hydroxyphthalimide (1.28 g, 7.85 mmol) and tetrahydrofuran (100 mL) was added diethyl azodicarboxylate (1.5 mL, 9.53 mmol). After stirred at room temperature overnight, the reaction solution was concentrated and flash chromatographed ($SiO_2$) to give the title compound as a yellow oil (2.84 g, 98.0%). $^1$H NMR ($CDCl_3$) δ7.85–7.81 (m, 2 H), 7.79–7.74 (m, 2 H), 7.35–7.29 (m, 5 H), 6.45 (s(b), 2 H), 5.77–5.75 (m, 1 H), 5.11–5.09 (m, 2 H), 4.61–4.58 (m, 1 H), 4.45–4.40 (m, 1 H), 4.16–4.08 (m, 1 H), 4.00–3.78 (m, 2 H), 3.62–3.46 (m, 2 H), 2.13–2.07 (m, 2 H), 1.78–1.47 (m, 6 H).

6. N-{1-[(1,3-Dioxoisoindolin-2-yloxy)methyl]-3-hydroxypropyl}(phenylmethoxy)carboxamide The product of the preceding step (290 mg, 0.620 mmol) in acetic acid (8 mL), tetrahydrofuran (4 mL) and water (2 mL) was heated at 55° C. for 3 h. After concentration and flash chromatography of the residue provided the title compound as a white solid (225 mg, 94.6%). $^1$H NMR ($CDCl_3$) δ7.87–7.84 (m, 2 H), 7.79–7.76 (m, 2 H), 7.39–7.35 (m, 5 H), 6.00–5.98 (m, 1 H), 5.20 (d, 1 H, J=12.3 Hz), 5.11 (d, 1 H, J=12.3 Hz), 4.45 (dd, 1 H, J=4.0, 9.8 Hz), 4.26–4.14 (m, 2 H), 3.80–3.70 (m, 2 H), 3.08–3.04 (m, 1 H), 2.02–1.79 (m, 2 H).

7. N-(1{[(tert-Butoxy)carbonylaminooxyl]methyl}-3-hydroxypropyl)(phenylmethoxy)carboxamide A solution of the product (4.10 g, 10.7 mmol), as prepared in the preceding step, tetrahydrofuran (40 mL), and methanol (40 mL) was treated with 40 wt. % methylamine in water (10 mL, 116 mmol) at room temperature for 1.5 h. The solvents were evaporated, and a white solid was filtered and washed with diethyl ether. The filtrate was concentrated to a yellow oil. To a solution of the yellow oil, sodium bicarbonate (1.80 g, 21.4 mmol), dichloromethane (40 mL) and water (30 mL) was added a solution of di-tert-butyldicarbonate (3.00 g, 13.7 mmol) in dichloromethane (8 mL) dropwise. After stirring at room temperature overnight, the organic phase was separated and the aqueous phase was extracted with dichloromethane. The organic layer was dried, concentrated, and flash chromatographed to provide the title compound as a white semi-solid (3.20 g, 84.7%, 2 steps). $^1$H NMR ($CDCl_3$) δ7.44 (s, 1 H), 7.37–7.30 (m, 5 H), 5.79 (d, 1 H, J=7.7 Hz), 5.13 (d, 2 H, J=3.1 Hz), 4.13–4.06 (m, 1 H), 3.98–3.89 (m, 2 H), 3.70 (m, 2 H), 1.85–1.78 (m, 1 H), 1.70–1.62 (m, 1 H), 1.47 (s, 9 H).

8. tert-Butyl 5-[(phenylmethoxy)carbonylamino]-1,2-oxazaperhydroine-2-carboxylate To a solution of the product (3.20 g, 9.04 mmol) of the preceding step, triphenylphosphine (5.21 g, 19.9 mmol) and tetrahydrofuran (120 mL) was added diethyl azodicarboxylate (3.2 mL, 20.3 mmol) at 4° C. After stirring at 4° C. to room temperature for 3 h, the solvent was evaporated and the residue was flash chromatographed to give the title compound as a yellow oil (2.50 g, 82.3%). $^1$H NMR ($CDCl_3$) δ7.40–7.30 (m, 5 H), 5.10 (s, 3 H), 4.16–4.08 (m, 1 H), 3.93 (m, 1 H), 3.75–3.63 (m, 3 H), 2.01–1.91 (m, 1 H), 1.70–1.64 (m, 1 H), 1.49 (s, 9 H). Mass spectrum (LCMS, ESI) calcd. for $C_{17}H_{24}N_2O_5$: 359 (M+Na). Found: 359.

9. N-(1,2-Oxazaperhydroin-5-yl)(phenylmethoxy)carboxamide

A solution of the product (2.30 g, 6.85 mmol) of the preceding step in trifluoroacetic acid (10 mL) and dichloromethane (30 mL) was stirred at room temperature for 1.5 h. After concentration in vacuo, the residue was partitioned between dichloromethane and saturated sodium bicarbonate. The organic phase was dried, concentrated, and flash chromatographed to give the title compound as a white solid (1.01 g, 62.5%). $^1$H NMR ($CDCl_3$) δ7.37–7.32 (m, 5 H), 5.10 (s, 2 H), 5.05–5.01 (m, 1 H), 4.07 (dd, 1 H, J=3.1, 11.4 Hz), 3.84 (m, 1 H), 3.62 (dd, 1 H, J=5.5, 11.3 Hz), 3.30–3.22 (m, 1H), 3.12–3.04 (m, 1 H), 2.05–1.98 (m, 1 H), 1.71–1.64 (m, 1 H).

10. tert-Butyl-2-aza-3-[(tert-butoxy)carbonylamino]-3-{5-[(phenylmethoxy)carbonylamino](1,2-oxazaperhydroin-2-yl)}prop-2-enoate The product (1.01 g, 4.28 mmol) of the preceding step in N,N-dimethylformamide (60 mL) was reacted with N,N'-bis(tert-butoxycarbonyl)-1H-pyrazole-1-carboxamidine (1.60 g, 5.16 mmol) at 45° C. overnight. The solvent was evaporated and the residue was flash chromatographed to yield the title compound as a clear oil (1.90 g, 92.9%). $^1$H NMR ($CDCl_3$) δ9.19 (s(b), 1 H), 7.62 (d, 1 H, J=2.1 Hz), 7.40–7.30 (m, 5 H), 5.10 (s, 2 H), 5.03 (d, 1 H, J=7.6 Hz), 4.24 (dd, 1 H, J=2.9, 11.3 Hz), 3.95 (m, 1 H), 3.86–3.80 (m, 3 H), 2.11–2.01 (m, 1 H), 1.81–1.70 (m, 1 H), 1.51 (s, 9 H), 1.49 (s, 9 H). Mass spectrum (LCMS, ESI) calcd. for $C_{23}H_{34}N_4O_7$: 479 (M=H). Found: 479.

11. 5-Amino-1,2-oxazaperhydroine-2-carboxamidine hydrobromide

The product (1.88 g, 3.93 mmol) of the preceding step was treated with 30 wt. % hydrobromic acid in acetic acid (60 mL) at room temperature for 3.5 h. The reaction solution was concentrated under reduced pressure, a mixture of solvents methanol, dichloromethane and hexane were added, and evaporated again to provide the title compound as a brown solid (1.41 g, quant. yield). $^1$H NMR (DMSO-$d_6$) δ8.31 (s, 3 H), 7.87 (s, 5 H), 4.21 (dd, 1 H, J=3.3, 12.0 Hz), 4.06–3.95 (m, 2 H), 3.82–3.76 (m, 1 H), 3.56–3.54 (m, 1 H), 2.14–2.08 (m, 1 H), 1.85–1.80 (m, 1 H). Mass spectrum (LCMS, ESI) calcd. for $C_5H_{12}N_4O$: 145 (M +H). Found: 145.

12. N-(2-{[(tert-Butoxy)carbonylamino]iminomethyl}(1,2-oxazaperhydroin-5-yl))-2-(6-methyl-3-{[(3-methylphenyl)sulfonyl]amino}-2-oxohydropyridyl)acetamide To a solution of 5-amino-1,2-oxazaperhydroine-2-carboxamidine hydrobromide (0.960 g, 3.14 mmol), as prepared in the preceding step, and 2-(6-methyl-3-{[(3-methylphenyl)sulfonyl]amino}-2-oxohydropyridyl)acetic acid (1.00 g, 2.98 mmol), as prepared in Example 1, step 5, in N,N-dimethylformamide (20 mL) was added N,N-diisopropylethylamine (2.30 g, 17.8 mmol) and Castro's reagent (1.45 g, 3.28 mmol) at 4° C. After the solution was stirred at 4° C. to room temperature overnight, di-tert-butyldicarbonate (1.30 g, 5.96 mmol) was added. After 3h at room temperature, the solution was concentrated and the residue was partitioned between dichloromethane and 10% citric acid (×2). The organic layer was dried, concentrated, and flash chromatographed to produce the title compound as a white solid (1.30 g, 77.7%). $^1$H NMR ($CDCl_3$) δ8.56 (s(b), 2 H), 7.65 (m, 2 H), 7.44 (d, 1 H, J=7.7 Hz) 7.32–7.30 (m, 2 H), 6.07 (d, 1 H, J=7.8 Hz), 4.75–4.62 (m, 2 H), 4.10–4.05 (m, 2 H), 3.90–3.88 (m, 1 H), 3.74–3.69 (m, 1 H), 2.38 (s, 3 H), 2.35 (s, 3 H), 1.89–1.82 (m, 1 H), 1.64–1.62 (m, 1 H), 1.46–1.42 (m, 1 H). Mass spectrum (LCMS, ESI) calcd. for $C_{25}H_{34}N_6O_7S$: 563 (M+H). Found: 563.

13. 5-[2-(6-Methyl-3-{[(3-methylphenyl)sulfonyl]amino}-2-oxohydropyridyl)-acetylamino]-1,2-oxazaperhydroine-2-carboxamidine trifluoroacetate A solution of the product (1.30 g, 2.31 mmol) of the preceding step in trifluoroacetic acid (10 mL) and dichloromethane (10 mL) was stirred at room temperature for 2.5 h. The solution was concentrated, a mixture of solvents methanol and dichloromethane were added and evaporated in vacuo again. To the residue was added dichloromethane, the solid was filtered and washed with dichloromethane and diethyl ether. The white solid was collected and dried on high vacuum pump to give the title compound (554 mg, 41.6%). $^1$H NMR (DMSO-$d_6$) δ9.27 (s, 1 H), 8.51 (d, 1 H, J=7.0 Hz), 7.84 (s, 4 H), 7.66–7.62 (m, 2 H), 7.43–7.41 (m, 2 H), 7.23 (d, 1 H, J=7.6 Hz), 6.53 (s(b), 1 H), 6.07 (d, 1H, J=7.7 Hz), 4.63 (s, 2 H), 4.08–3.96 (m, 3 H), 3.75–3.65 (m, 2 H), 2.35 (s, 3 H), 2.18 (s, 3 H), 1.98–1.92 (m, 1 H), 1.68–1.63 (m, 1 H). Mass spectrum (LCMS ESI) calcd. for $C_{20}H_{26}N_6O_5S$: 463 (M=H).
Found.463.

EXAMPLE 3

In vitro Inhibition of Purified Thrombin

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.). Human α-thrombin, was obtained from Enzyme Research Laboratories (South Bend, Ind.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for>15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human a-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 mM.

The compound of Example 1 had a thrombin inhibitory activity of 26 nM. The compound of Example 2 had a thrombin inhibitory activity of 0.38 nM. The results indicate that the compounds of the present invention are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A compound having the Formula VII:

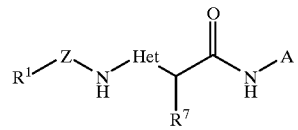

VII or a solvate, hydrate or pharmaceutically acceptable salt thereof; wherein:

A is one of

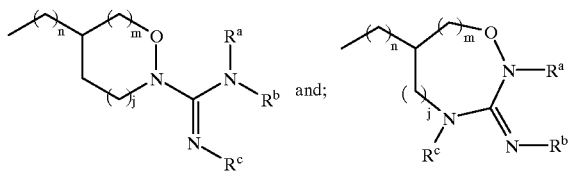

$R^1$ is alkyl, cycloalkyl, cycloalkylalkyl, alkenyl, alkynyl, aryl, aralkyl, thienyl, thienyl($C_{1-4}$)alkyl, quinolinyl, quinolinyl($C_{1-4}$)alkyl, imidazolyl, imidazolyl($C_{1-4}$) alkyl, pyridyl, or pyridyl($C_{1-4}$)alkyl, any of which may be optionally substituted;

Z is —$SO_2$—,—OCO—,—CO—, —$NR^2CO$— or a covalent bond,
where $R^2$ is hydrogen, alkyl, aralkyl, aryl, hydroxy ($C_{2-10}$)alkyl, amino($C_{2-10}$)alkyl, monoalkylamino ($C_{2-10}$)alkyl, dialkylamino($C_{2-10}$)alkyl or carboxyalkyl;

Het is

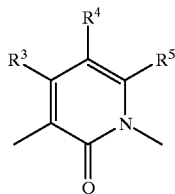
A where
R³, R⁴ and R⁵ are independently hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, alkoxycarbonylmethyl, carboxymethyl, —CO₂R$^x$, —CH₂OR$^x$ or —OR$^x$,
where R$^x$, in each instance, is independently one of hydrogen, alkyl or cycloalkyl wherein said alkyl or cycloalkyl groups may optionally have one or more unsaturations;
R⁷ is hydrogen, $C_{1-4}$alkyl, or $C_{2-4}$ alkenyl;
R$^a$, R$^b$ and R$^c$ are independently hydrogen, alkyl, hydroxy, alkoxy, aryloxy, aralkoxy, alkoxycarbonyloxy, cyano or —CO₂R$^w$, where R$^w$ is alkyl, cycloalkyl, phenyl, benzyl,

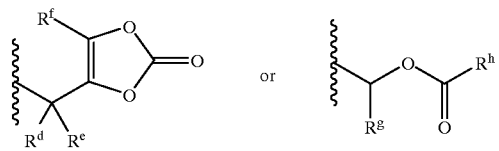

where
R$^d$ and R$^e$ are independently hydrogen, $C_{1-6}$ alkyl, $C_{2-6}$ alkenyl or phenyl, R$^f$ is hydrogen, $C_{1-6}$ alkyl, $C_{2-6}$ alkenyl or phenyl, R$^g$ is hydrogen, $C_{1-6}$ alkyl, $C_{2-6}$ alkenyl or phenyl, and R$^h$ is aralkyl or $C_{1-6}$ alkyl;
each n is zero or 1;
each m is zero or 1; and
each j is zero or 1;
provided that n, m and j are not all zero.

2. A compound of claim 1, wherein R¹ is $C_{6-10}$ ar($C_{1-4}$)alkyl, $C_{6-10}$ aryl, $C_{4-7}$ cycloalkyl($C_{1-4}$)alkyl, thienyl, thienyl ($C_{1-4}$)alkyl, quinolinyl, quinolinyl($C_{1-4}$)alkyl, imidazolyl, imidazolyl($C_{1-4}$)alkyl, pyridyl, or pyridyl($C_{1-4}$)alkyl, any of which is optionally substituted.

3. A compound of claim 2, wherein R¹ is $C_{6-10}$ ar($C_{1-4}$)alkyl, $C_{6-10}$, aryl, $C_{4-7}$ cycloalky($C_{1-4}$)alkyl, any of which is optionally substituted by 1–5 of hydroxy, nitro, trifluoromethyl, halogen, $C_{1-6}$ alkyl, $C_{2-6}$ alkenyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$)alkylamino, di($C_{1-4}$) alkylamino, $C_{2-6}$ alkylcarbonylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy($C_{2-6}$) alkoxy, mono- and di-$C_{1-4}$ alkylamino ($C_{2-6}$)alkoxy, $C_{2-10}$ mono(carboxyalkyl)amino, bis($C_{2-10}$ carboxyalkyl) amino, $C_{6-14}$ ar($C_{1-6}$) alkoxycarbonyl, $C_{2-6}$ alkynylcarbonyl, $C_{1-6}$ alkylsulfonyl, $C_{2-6}$ alkenylsulfonyl, $C^{2-6}$ alkynylsulfonyl, $C_{6-10}$ arylsulfonyl, $C_{6-10}$ ar($C_{1-6}$) alkylsulfonyl, $C_{1-6}$ alkylsulfonyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy.

4. A compound of claim 1, wherein Het is

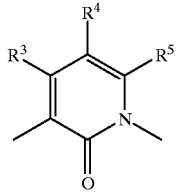

where R³, R⁴ and R⁵ are independently hydrogen, $C_{1-4}$ alkyl, $C_{3-7}$ cycloalkyl, $C_{6-14}$ aryl, $C_{6-10}$ ar($C_{1-4}$)alkyl, trifluoromethyl, halogen, hydroxyalkyl, cyano, nitro, carboxamido, carboxy, alkoxycarbonyl, carboxymethyl, alkoxycarbonylmethyl, or cycloalkyloxycarbonyl.

5. A compound of claim 4, wherein R³, R⁴ and R⁵ are independently hydrogen, methyl, ethyl, propyl, chloro, bromo, trifluoromethyl, hydroxymethyl, methoxy, ethoxy, carboxamido, nitro, phenyl, cyclopropyl, hydroxy, isopropyl, methoxycarbonyl, ethoxycarbonyl and benzyl.

6. A compound of claim 1, wherein R³ and R⁴ groups are independently hydrogen, $C_{1-12}$ alkyl, or $C_{2-6}$ alkenyl.

7. A compound of claim 6, wherein R³ and R⁴ are hydrogen.

8. A compound of claim 6, wherein R⁵ is hydrogen, halogen, $C_{1-5}$ alkyl, $C_{3-6}$ alkenyl, $C_{3-5}$ cycloalkyl, trifluoromethyl, or $C_{1-4}$ alkoxy.

9. A compound of claim 1, wherein Het is:

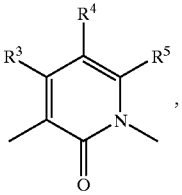

wherein
R³ and R⁴ are independently selected to be hydrogen or methyl, and
R⁵ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, and S-3-hexyl.

10. A compound of claim 9, wherein R⁵ is hydrogen, methyl, ethyl, propyl or isopropyl.

11. A compound of claim 1, wherein Z is —SO₂— or a covalent bond.

12. A compound of claim 1, wherein R⁷ is hydrogen.

13. A compound of claim 1, wherein
R$^a$, R$^b$ and R$^c$ are independently hydrogen, hydroxy, $C_{1-6}$ alkyl, $C_{1-6}$ alkoxy, cyano or —CO₂R$^w$, where R$^w$, in each instance, is one of $C_{1-4}$alkyl, $C_{4-7}$cycloalkyl or benzyl,

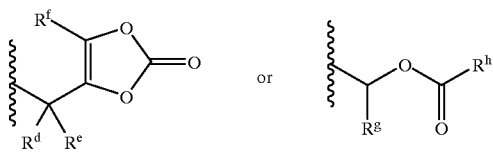

where
Rᵈ, Rᵉ and Rᵍ are hydrogen,
Rᶠ is methyl, and
Rʰ is benzyl or tert-butyl.

14. A compound of claim 13, wherein
Rᵃ, Rᵇ and Rᶜ are hydrogen, methyl, ethyl, propyl, n-butyl, hydroxy, methoxy, ethoxy, cyano, —CO₂CH₃, —CO₂CH₂CH₃ and —CO₂CH₂CH₂CH₃.

15. A compound of claim 14, wherein Rᵃ, Rᵇ and Rᶜ are each hydrogen.

16. A compound of claim 1, wherein:
$R^1$ is $C_{6-10}$ ar($C_{1-4}$) alkyl, $C_{6-10}$ aryl, $C_{4-7}$ cycloalkyl($C_{1-4}$)alkyl, any of which is optionally substituted by 1–5 of hydroxy, nitro, trifluoromethyl, halogen, $C_{1-6}$ alkyl, $C_{6-10}$ aryl, $C_{1-6}$ alkoxy, $C_{6-10}$ ar($C_{1-6}$)alkoxy, $C_{1-6}$ aminoalkyl, $C_{1-6}$ aminoalkoxy, amino, mono($C_{1-4}$) alkylamino, di($C_{1-4}$)alkylamino, $C_{2-6}$ alkoxycarbonylamino, $C_{2-6}$ alkoxycarbonyl, carboxy, $C_{1-6}$ hydroxyalkyl, $C_{2-6}$ hydroxyalkoxy, ($C_{1-6}$)alkoxy ($C_{2-6}$)alkoxy, mono- and di-$C_{1-4}$ alkylamino ($C_{2-6}$) alkoxy, $C_{2-10}$ mono(carboxyalkyl)amino, bis($C_{2-10}$ carboxyalkyl)amino, $C_{6-14}$ ar($C_{1-6}$) alkoxycarbonyl, $C_{2-6}$ alkynylcarbonyl, $C_{2-6}$ alkylsulfonyl, $C_{1-6}$ alkenylsulfonyl, $C_{2-6}$ alkynylsulfonyl, $C_{6-10}$ arylsulfonyl, $C_{6-10}$ ar($C_{1-6}$) alkylsulfonyl, $C_{1-6}$ alkylsulfinyl, $C_{1-6}$ alkylsulfonamido, $C_{6-10}$ arylsulfonamido, $C_{6-10}$ ar($C_{1-6}$) alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, or perfluoroethoxy;
Het is:

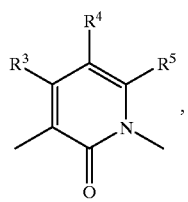

wherein
R³ and R⁴ are independently selected to be hydrogen or methyl, and
R⁵ is selected from the group consisting of hydrogen, methyl, ethyl, propenyl, allyl, propyl, isopropyl, butyl, R-sec-butyl, S-sec-butyl, isobutyl, 1-pentyl, R-2-pentyl, S-2-pentyl, 3-pentyl, S-1-(2-methyl)-butyl, R-2-(3-methyl)-butyl, 1-(3-methyl)-butyl, R-1-(2-methyl)-butyl, cyclopentyl, 2-pyrrolyl, 3-pyrrolyl, 1-hexyl, S-2-hexyl, R-2-hexyl, R-3-hexyl, and S-3-hexyl;
Z is —SO₂— or a covalent bond;
R⁷ is hydrogen or $C_{1-4}$ alkyl;
Rᵃ, Rᵇ and Rᶜ are hydrogen, methyl, ethyl, propyl, n-butyl, hydroxy, methoxy, ethoxy, cyano, —CO₂CH₃, —CO₂CH₂CH₃ and —CO₂CH₂CH₂CH₃.

17. A compound of claim 1, wherein
Z is —SO₂—,
R¹ is substituted or unsubstituted aryl or aralkyl,
Het is

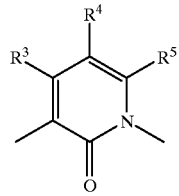

Rᵃ, Rᵇ and Rᶜ are all hydrogen.
18. A compound of claim 17, wherein
R¹ is substituted or unsubstituted benzyl or phenyl.
19. A compound having Formula VIII:

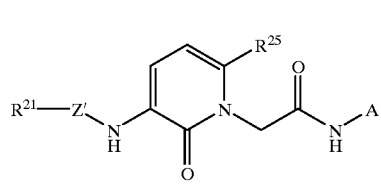

VIII or a solvate, hydrate of pharmaceutically acceptable salt thereof; wherein
Z' is —OCO—, —CO—, —SO₂—, —NHCO—, or a covalent bond;
$R^{21}$ is:
$R^{22}(CH_2)_k$, where k is 0–4, $(R^{22})(OR^{22})CH(CH_2)_p$, where p is 1–4,
$(R^{22})_2CH(CH_2)_k$, where k is 0–4 and $R^{22}$ can be the same or different, and wherein $(R^{22})_2$ can also be a ring substituent on CH represented by $C_{3-7}$ cycloalkyl or $C_{7-12}$ bicyclic alkyl, and
$R^{22}O(CH_2)_p$, wherein p is 1–4,
$R^{22}$ is hydrogen; phenyl, unsubstituted or substituted with one or more of $C_{1-4}$ alkyl, $C_{1-4}$ alkoxy, halogen, trifluoromethyl, hydroxy, COOH, or CONH₂; naphthyl; biphenyl; $C_{1-4}$ alkyl; $C_{3-7}$ cycloalkyl, or $C_{7-12}$ bicyclic alkyl;
$R^{25}$ is hydrogen; $C_{1-4}$ alkyl; $C_{3-7}$ cycloalkyl, or trifluoromethyl; and wherein Rᵃ, Rᵇ and Rᶜ are independently hydrogen, hydroxy, or cyano.
20. A compound of claim 19, wherein Z' is a covalent bond or —SO₂—.
21. A compound of claim 19, wherein $R^{21}$ is $R^{22}(CH_2)_k$, $(R^{22})_2CH(CH_2)_k$, phenyl, or (phenyl)₂—CH.
22. A compound of claim 19, wherein $R^{25}$ is $C_{1-4}$ alkyl.
23. A compound of claim 22, wherein $R^{25}$ is methyl.
24. A compound of claim 1, wherein
R¹ is phenyl, benzyl, 1-naphtylmethyl, 2-naphthylmethyl, pyridyl, pyridylmethyl, quinolinyl or quinolinylmethyl, any of which is optionally substituted by 1–5 of chloro, methoxy, methyl, trifluoromethyl, cyano, nitro, methylsulfonyl, amino or dimethylamino.
25. A compound of claim 1, wherein
R¹ is 8-quinolinyl, 5-methyl-8-quinolinyl, 8-quinolinylmethyl, 5-methyl-8-quinolinylmethyl, 4-benzo-2,1,3-thiadiazolyl, 5-chloro-2-thiophenyl, 5-chloro-1,3-dimethyl-4-pyrazolyl, pyridyl, isoquinolinyl, pyridylmethyl, isoquinolinylmethyl, tetrahydroquinolinyl and tetrahydroquinolinylmethyl.

26. A compound of claim 1, which is one of:
N-[(3-Imino(1,2,4-oxadiazaperhydroin-6-yl))methyl]-2-(6-methyl-3-{[(3-methylphenyl)sulfonyl]amino}-2-oxohydropyridyl)acetamide trifluoroacetate, or
5-[2-(6-Methyl-3-{[(3-methylphenyl)sulfonyl]amino}-2-oxohydropyridyl)acetylamino]-1,2-oxazaperhydroine-2-carboxamidine trifluoroacetate;
or a pharmaceutically acceptable salt thereof.

27. A compound of claim 1, which is

5-[2-(6-methyl-3-{benzylsulfonylamino}-2-oxohydropyridyl)acetylamino]-1,2-oxazaperhydroine-2-carboxamidine;
5-[2-({3-benzylsulfonylamino}-2-oxohydropyridyl)acetylamino]-1,2,-oxazaperhydroine-2-carboxamidine;
5-[2-(6-methyl-3-{benzylsulfonylamino}-2-oxohydropyridyl)acetylamino]-1,2-oxazaperhydroine-2-carboxamidine;
5-[2-(6-methyl-3-{(3-methylphenyl)sulfonylamino}-2-oxohydropyridyl)acetylamino]-1,2-oxazaperhydroine-2-carboxamidine;
5-[2-(6-methyl-3-{benzyloxycarbonylamino}-2-oxohydropyridyl)acetylamino]-1,2-oxazaperhydroine-2-carboxamidine;
5-[2-(6-methyl-3-{3-chlorobenzylsulfonylamino}-2-oxohydropyridyl)acetylaminol]-1,2-oxazaperhydroine-2-carboxamidine;
5-[2-(6-methyl-3-{3-fluoromethylbenzylsulfonylamino}-2-oxohydropyridyl)acetylamino]-1,2-oxazaperhydroine-2-carboxamidine;
5-[2-(6-methyl-3-{2-iodobenzylsulfonylamino}-2-oxohydropyridyl)acetylamino]-1,2-oxazaperhydroine-2-carboxamidine;
5-[2-(6-methyl-3-{2-chlorobenzylsulfonylamino}-2-oxohydropyridyl)acetylamino]-1,2-oxazaperhydroine-2-carboxamidine;
5-[2-(6-methyl-3-{2-bromobenzylsulfonylamino}-2-oxohydropyridyl)acetylamino]-1,2-oxazaperhydroine-2-carboxamidine;
5-[2-(6-methyl-3-{3-fluorobenzylsulfonylamino}-2-oxohydropyridyl)acetylamino]-1,2-oxazaperhydroine-2-carboxamidine;
5-[2-(6-methyl-3-{4-chlorobenzylsulfonylamino}-2-oxohydropyridyl)acetylamino]-1,2-oxazaperhydroine-2-carboxamidine;
5-[2-(6-methyl-3-{2-chloro-6-fluorobenzylsulfonylamino}-2-oxohydropyridyl)acetylamino]-1,2-oxazaperhydroine-2-carboxamidine;
5-[2-(6-methyl-3-{2-fluorobenzylsulfonylamino}-2-oxohydropyridyl)acetylamino]-1,2-oxazaperhydroine-2-carboxamidine;
5-[2-(6-methyl-3-{2,3-dichlorobenzylsulfonylamino}-2-oxohydropyridyl)acetylamino]-1,2-oxazaperhydroine-2-carboxamidine;
5-[2-(6-methyl-3-{3,4-difluorobenzylsulfonylamino}-2-oxohydropyridyl)acetylamino]-1,2-oxazaperhydroine-2-carboxamidine;
5-[2-(6-methyl-3-{2,4-dichlorobenzylsulfonylamino}-2-oxohydropyridyl)acetylamino]-1,2-oxazaperhydroine-2-carboxamidine;
5-[2-(6-methyl-3-{3-chlorophenylsulfonylamino}-2-oxohydropyridyl)acetylamino]-1,2-oxazaperhydroine-2-carboxamidine;
5-[2-(6-methyl-3-{(3-bromophenyl)sulfonylamino}-2-oxohydropyridyl)acetylamino]-1,2-oxazaperhydroine-2-carboxamidine;
5-[2-(6-methyl-3-{(3-fluorophenyl)sulfonylamino}-2-oxohydropyridyl)acetylamino]-1,2-oxazaperhydroine-2-carboxamidine;
5-[2-(6-methyl-3-{naphthalen-1-ylsulfonylamino}-2-oxohydropyridyl)acetylamino]-1,2-oxazaperhydroine-2-carboxamidine;
5-[2-(6-methyl-3-{naphthalen-2-ylsulfonylamino}-2-oxohydropyridyl)acetylamino]-1,2-oxazaperhydroine-2-carboxamidine;
5-[2-(6-methyl-3-{(2-chlorophenyl)sulfonylamino}-2-oxohydropyridyl)acetylamino]-1,2-oxazaperhydroine-2-carboxamidine;
5-[2-(6-methyl-3-{(4-chlorophenyl)sulfonylamino}-2-oxohydropyridyl)acetylamino]-1,2-oxazaperhydroine-2-carboxamidine;
5-[2-(6-methyl-3-{phenylsulfonamido}-2-oxohydropyridyl)acetylamino]-1,2-oxazaperhydroine-2-carboxamidine;
5-[2-(6-methyl-3-{naphthalen-1 -ylmethylsulfonylamino}-2-oxohydropyridyl)acetylamino]-1,2-oxazaperhydroine-2-carboxamidine;
5-[2-(6-methyl-3-{naphthalen-2-ylmethylsulfonylamino}-2-oxohydropyridyl)acetylamino]-1,2-oxazaperhydroine-2-carboxamidine;
5-[2-(6-methyl-3-{(4-bromophenyl)sulfonylamino}-2-oxohydropyridyl)acetylamino]-1,2-oxazaperhydroine-2-carboxamidine;
5-[2-(6-methyl-3-{(4-fluorophenyl)sulfonylamino}-2-oxohydropyridyl)acetylamino]-1,2-oxazaperhydroine-2-carboxamidine;
5-[2-(6-methyl-3-{(4-iodophenyl)sulfonylamino}-2-oxohydropyridyl)acetylamino]-1,2-oxazaperhydroine-2-carboxamidine;
5-[2-(6-methyl-3-{(4-methoxyphenyl)sulfonylamino}-2-oxohydropyridyl)acetylamino]-1,2-oxazaperhydroine-2-carboxamidine;
5-[2-(6-methyl-3-{(3-trifluoromethylphenyl)sulfonylamino}-2-oxohydropyridyl)acetylamino]-1,2-oxazaperhydroine-2-carboxamidine;
5-[2-(6-methyl-3-{(4-isopropylphenyl)sulfonylamino}-2-oxohydropyridyl)acetylamino]-1,2-oxazaperhydroine-2-carboxamidine;
5-[2-(6-methyl-3-{(3,4-dimethoxyphenyl)sulfonylamino}-2-oxohydropyridyl)acetylamino]-1,2-oxazaperhydroine-2-carboxamidine;
5-[2-(6-methyl-3-{thien-2-ylsulfonylamino}-2-oxohydropyridyl)acetylamino]-1,2-oxazaperhydroine-2-carboxamidine;
5-[2-(6-methyl-3-{(4-vinylphenylsulfonyl)amino}-2-oxohydropyridyl)acetylamino]-1,2-oxazaperhydroine-2-carboxamidine;
5-[2-(6-methyl-3-{(2-butoxy-5-(1,1-dimethylpropyl)phenylsulfonyl)amino}-2-oxohydropyridyl)acetylamino]-1,2-oxazaperhydroine-2-carboxamidine;
5-[2-(6-methyl-3-{(3-nitrophenyl)sulfonylamino}-2-oxohydropyridyl)acetylamino]-1,2-oxazaperhydroine-2-carboxamidine;
5-[2-(6-methyl-3-{(4-methylcarbonylaminophenyl)sulfonylamino}-2-oxohydropyridyl)acetylamino]-1,2-oxazaperhydroine-2-carboxamidine;
5-[2-(6-methyl-3-{(4-tert-butylphenyl)sulfonylamino}-2-oxohydropyridyl)acetylamino]-1,2-oxazaperhydroine-2-carboxamidine;
5-[2-(6-methyl-3-{(3-cyanophenyl)sulfonylamino}-2-oxohydropyridyl)acetylamino]-1,2-oxazaperhydroine-2-carboxamidine;
5-[2-(6-methyl -3-{(4-methylsulfonylphenyl)sulfonylamino}-2-oxohydropyridyl)acetylamino]-1,2-oxazaperhydroine-2-carboxamidine;
5-[2-(6-methyl-3-{dansylamino}-2-oxohydropyridyl)acetylamino]-1,2-oxazaperhydroine-2-carboxamidine;

5-[2-(6-methyl-3-{pentafluorophenyl)sulfonylamino}-2-oxohydropyridyl)acetylamino]-1,2-oxazaperhydroine-2-carboxamidine;

5-[2-(6-methyl-3-{(2-methoxy-5-methylphenyl)sulfonylamino}-2-oxohydropyridyl)acetylamino]-1,2-oxazaperhydroine-2-carboxamidine;

5-[2-(6-methyl-3-{(4-phenylphenyl)sulfonylamino}-2-oxohydropyridyl)acetylamino]-1,2-oxazaperhydroinc-2-carboxamidine;

5-[2-(6-methyl-3-{(5-chlorothien-2-yl)sulfonylamino}-2-oxohydropyridyl)acetylamino]-1,2-oxazaperhydroine-2-carboxamidine;

5-[2-(6-methyl-3-{quinolin-8-ylsulfonylamino}-2-oxohydropyridyl)acetylamino]-1,2-oxazaperhydroine-2-carboxamidine;

5-[2-(6-methyl-3-{quinolin-5-ylsulfonylamino}-2-oxohydropyridyl)acetylamino]-1,2-oxazaperhydroine-2-carboxamidine;

5-[2-(6-methyl-3-{1-methylimidazol-4-ylsulfonylamino}-2-oxohydropyridyl)acetylamino]-1,2-oxazaperhydroine-2-carboxamidine;

5-[2-(6-methyl-3-{3-methylquinolin-8-ylsulfonylamino}-2-oxohydropyridyl)acetylamino]-1,2-oxazaperhydroine-2-carboxamidine;

5-[2-(6-methyl-3-{pyridin-2-ylsulfonylamino}-2-oxohydropyridyl)acetylamino]-1,2-oxazaperhydroine-2-carboxamidine;

5-[2-(6-methyl-3-{pyridin-3-ylsulfonylamino}-2-oxohydropyridyl)acetylamino]-1,2-oxazaperhydroine-2-carboxamidine;

5-[2-(6-isopropyl-3-{3-methylphenylsulfonylamino}-2-oxohydropyridyl)acetylamino]-1,2-oxazaperhydroine-2-carboxamidine;

5-[2-(6-ethyl-3-{3-methylphenylsulfonylamino}-2-oxohydropyridyl)acetylamino]-1,2-oxazaperhydroine-2-carboxamidine; or 5-[2-(6-propyl-3-{3-methylphenylsulfonylamino}-2-oxohydropyridyl)acetylamino]-1,2-oxazaperhydroine-2-carboxamidine; or a solvate, hydrate or pharmaceutically acceptable salt thereof.

28. A compound of claim 1, which is:

N-[3-imino-(1,2,4-oxadiazaperhydroin-6-yl)methyl]-2-(6-methyl-3-{benzylsulfonylamino}-2-oxohydropyridyl)acetamide;

N-[3-imino-(1,2,4-oxadiazaperhydroin-6-yl)methyl]-2-({3-benzylsulfonylamino}-2-oxohydropyridyl)acetamide;

N-[3-imino-(1,2,4-oxadiazaperhydroin-6-yl)methyl]-2-(6-methyl-3-{benzylsulfonylamino}-2-oxohydropyridyl)acetamide;

N-[3-imino-(1,2,4-oxadiazaperhydroin-6-yl)methyl]-2-(6-methyl-3-{(3-methylphenyl)sulfonylamino}-2-oxohydropyridyl)acetamide;

N-[3-imino-(1,2,4-oxadiazaperhydroin-6-yl)methyl]-2-(6-methyl-3-{benzyloxycarbonylamino}-2-oxohydropyridyl)acetamide;

N-[3-imino-(1,2,4-oxadiazaperhydroin-6-yl)methyl]-2-(6-methyl-3-{3-chlorobenzylsulfonylamino}-2-oxohydropyridyl)acetamide;

N-[3-imino-(1,2,4-oxadiazaperhydroin-6-yl)methyl]-2-(6-methyl-3-{3-trifluoromethylbenzylsulfonylamino}-2-oxohydropyridyl)acetamide;

N-[3-imino-(1,2,4-oxadiazaperhydroin-6-yl)methyl]-2-(6-methyl-3-{2-iodobenzylsulfonylamino}-2-oxohydropyridyl)acetamide;

N-[3-imino-(1,2,4-oxadiazaperhydroin-6-yl)methyl]-2-(6-methyl-3-{2-chlorobenzylsulfonylamino}-2-oxohydropyridyl)acetamide;

N-[3-imino-(1,2,4-oxadiazaperhydroin-6-yl)methyl]-2-(6-methyl-3-{2-bromobenzylsulfonylamino}-2-oxohydropyridyl)acetamide;

N-[3-imino-(1,2,4-oxadiazaperhydroin-6-yl)methyl]-2-(6-methyl-3-{3-fluorobenzylsulfonylamino}-2-oxohydropyridyl)acetamide;

N-[3-imino-(1,2,4-oxadiazaperhydroin-6-yl)methyl]-2-(6-methyl-3-{4-chlorobenzylsulfonylamino}-2-oxohydropyridyl)acetamide;

N-[3-imino-(1,2,4-oxadiazaperhydroin-6-yl)methyl]-2-(6-methyl-3-{2-chloro-6-fluorobenzylsulfonylamino}-2-oxohydropyridyl)acetamide;

N-[3-imino-(1,2,4-oxadiazaperhydroin-6-yl)methyl]-2-(6-methyl-3-{-2-fluorobenzylsulfonylamino}-2-oxohydropyridyl)acetamide;

N-[3-imino-(1,2,4-oxadiazaperhydroin-6-yl)methyl]-2-(6-methyl-3-{2,3-dichlorobenzylsulfonylamino}-2-oxohydropyridyl)acetamide;

N-[3-imino-(1,2,4-oxadiazaperhydroin-6-yl)methyl]-2-(6-methyl-3-{3,4-difluorobenzylsulfonylamino}-2-oxohydropyridyl)acetamide;

N-[3-imino-(1,2,4-oxadiazaperhydroin-6-yl)methyl]-2-(6-methyl-3-{2,4-dichlorobenzylsulfonylamino}-2-oxohydropyridyl)acetamide;

N-[3-imino-(1,2,4-oxadiazaperhydroin-6-yl)methyl]-2-(6-methyl-3-{3-chlorophenylsulfonylamino}-2-oxohydropyridyl)acetamide;

N-[3-imino-(1,2,4-oxadiazaperhydroin-6-yl)methyl]-2-(6-methyl-3-{(3-bromophenyl)sulfonylamino}-2-oxohydropyridyl)acetamide;

N-[3-imino-(1,2,4-oxadiazaperhydroin-6-yl)methyl]-2-(6-methyl-3-{(3-fluorophenyl)sulfonylamino}-2-oxohydropyridyl)acetamide;

N-[3-imino-(1,2,4-oxadiazaperhydroin-6-yl)methyl]-2-(6-methyl-3-{naphthalen-1-ylsulfonylamino}-2-oxohydropyridyl)acetamide;

N-[3-imino-(1,2,4-oxadiazaperhydroin-6-yl)methyl]-2-(6-methyl-3-{naphthalen-2-ylsulfonylamino}-2-oxohydropyridyl)acetamide;

N-[3-imino-(1,2,4-oxadiazaperhydroin-6-yl)methyl]-2-(6-methyl-3-{(2-chlorophenyl)sulfonylamino}-2-oxohydropyridyl)acetamide;

N-[3-imino-(1,2,4-oxadiazaperhydroin-6-yl)methyl]-2-(6-methyl-3-{(4-chlorophenyl)sulfonylamino}-2-oxohydropyridyl)acetamide;

N-[3-imino-(1,2,4-oxadiazaperhydroin-6-yl)methyl]-2-(6-methyl-3-{phenylsulfonylamino}-2-oxohydropyridyl)acetamide;

N-[3-imino-(1,2,4-oxadiazaperhydroin-6-yl)methyl]-2-(6-methyl-3-{naphthalen-1-ylmethylsulfonylamino}-2-oxohydropyridyl)acetamide;

N-[3-imino-(1,2,4-oxadiazaperhydroin-6-yl)methyl]-2-(6-methyl-3-{naphthalen-2-ylmethylsulfonylamino}-2-oxohydropyridyl)acetamide;

N-[3-imino-(1,2,4-oxadiazaperhydroin-6-yl )methyl]-2-(6-methyl-3-{(4-bromophenyl)sulfonylamino}-2-oxohydropyridyl)acetamide;

N-[3-imino-(1,2,4-oxadiazaperhydroin-6-yl)methyl]-2-(6-methyl-3-{(4-fluorophenyl)sulfonylamino}-2-oxohydropyridyl)acetamide;

N-[3-imino-(1,2,4-oxadiazaperhydroin-6-yl)methyl]-2-(6-methyl-3-{(4-iodophenyl)sulfonylamino}-2-oxohydropyridyl)acetamide;

N-[3-imino-(1,2,4-oxadiazaperhydroin-6-yl)methyl]-2-(6-methyl-3-{(4-methoxyphenyl)sulfonylamino}-2-oxohydropyridyl)acetamide;

N-[3-imino-(1,2,4-oxadiazaperhydroin-6-yl)methyl]-2-(6-methyl-3-{(3-trifluoromethylphenyl)sulfonylamino}-2-oxohydropyridyl)acetamide;

N-[3-imino-(1,2,4-oxadiazaperhydroin-6-yl)methyl]-2-(6-methyl-3-{(4-isopropylphenyl)sulfonylamino}-2-oxohydropyridyl)acetamide;

N-[3-imino-(1,2,4-oxadiazapehydroin-6-yl)methyl]-2-(6-methyl-3-{(3,4-dimethoxyphenyl)sulfonylamino}-2-oxohydropyridyl)acetamide;

N-[3-imino-(1,2,4-oxadiazaperhydroin-6-yl)methyl]-2-(6-methyl-3-{thien-2-ylsulfonylamino}-2-oxohydropyridyl)acetamide;

N-[3-imino-(1,2,4-oxadiazaperhydroin-6-yl)methyl]-2-(6-methyl-3-{(4-vinylphenylsulfonyl)amino}-2-oxohydropyridyl)acetamide;

N-[3-imino-(1,2,4-oxadiazaperhydroin-6-yl)methyl]-2-(6-methyl-3-{(2-butoxy-5-(1,1-dimethylpropyl)phenylsulfonyl)amino}-2-oxohydropyridyl)acetamide;

N-[3-imino-(1,2,4-oxadiazaperhydroin-6-yl)methyl]-2-(6-methyl-3-{(3-nitrophenyl)sulfonylamino}-2-oxohydropyridyl)acetamide;

N-[3-imino-(1,2,4-oxadiazaperhydroin-6-yl)methyl]-2-(6-methyl-3-{(4-methylcarbonylaminophenyl)sulfonylamino}-2-oxohydropyridyl)acetamide;

N-[3-imino-(1,2,4-oxadiazaperhydroin-6-yl)methyl]-2-(6-methyl-3-{(4-tert-butylphenyl)sulfonylamino}-2-oxohydropyridyl)acetamide;

N-[3-imino-(1,2,4-oxadiazaperhydroin-6-yl)methyl]-2-(6-methyl-3-{(3-cyanophenyl)sulfonylamino}-2-oxohydropyridyl)acetamide;

N-[3-imino-(1,2,4-oxadiazaperhydroin-6-yl)methyl]-2-(6-methyl-3-{(4-methylsulfonylphenyl)sulfonylamino}-2-oxohydropyridyl)acetamide;

N-[3-imino-(1,2,4-oxadiazaperhydroin-6-yl)methyl]-2-(6-methyl-3{dansylamino)}-2-oxohydropyridyl)acetamide;

N-[3-imino-(1,2,4-oxadiazaperhydroin-6-yl)methyl]-2-(6-methyl-3-{pentafluorophenyl)sulfonylamino}-2-oxohydropyridyl)acetamide;

N-[3-imino-(1,2,4-oxadiazaperhydroin-6-yl)methyl]-2-(6-methyl-3-{(2-methoxy-5-methylphenyl)sulfonylamino}-2-oxohydropyridyl)acetamide;

N-[3-imino-(1,2,4-oxadiazaperhydroin-6-yl)methyl]-2-(6-methyl-3-{(4-phenylphenyl)sulfonylamino}-2-oxohydropyridyl)acetamide;

N-[3-imino-(1,2,4-oxadiazaperhydroin-6-yl)methyl]-2-(6-methyl-3-{(5-chlorothien-2-yl)sulfonylamino}-2-oxohydropyridyl)acetamide;

N-[3-imino-(1,2,4-oxadiazaperhydroin-6-yl)methyl]-2-(6-methyl-3-{quinolin-8-ylsulfonylamino}-2-oxohydropyridyl)acetamide;

N-[3-imino-(1,2,4-oxadiazaperhydroin-6-yl)methyl]-2-(6-methyl-3-{quinolin-5-ylsulfonylamino}-2-oxohydropyridyl)acetamide;

N-[3-imino-(1,2,4-oxadiazaperhydroin-6-yl)methyl]-2-(6-methyl-3-{1-methylimidazol-4-ylsulfonylamino}-2-oxohydropyridyl)acetamide;

N-[3-imino-(1,2,4-oxadiazaperhydroin-6-yl)methyl]-2-(6-methyl-3-{3-methylquinolin-8-ylsulfonylamino}-2-oxohydropyridyl)acetamide;

N-[3-imino-(1,2,4-oxadiazaperhydroin-6-yl)methyl]-2-(6-methyl-3-{pyridin-2-ylsulfonylamino}-2-oxohydropyridyl)acetamide;

N-[3-imino-(1,2,4-oxadiazaperhydroin-6-yl)methyl]-2-(6-methyl-3-{pyridin-3-ylsulfonylamino}-2-oxohydropyridyl)acetamide;

N-[3-imino-(1,2,4-oxadiazaperhydroin-6-yl)methyl]-2-(6-isopropyl-3-{3-methylphenylsulfonylamino}-2-oxohydropyridyl)acetamide;

N-[3-imino-(1,2,4-oxadiazaperhydroin-6-yl)methyl]-2-(6-ethyl-3-{3-methylphenylsulfonylamino}-2-oxohydropyridyl)acetamide; or N-[3-imino-(1,2,4-oxadiazaperhydroin-6-yl)methyl]-2-(6-propyl-3-{3-methylphenylsulfonylamino}-2-oxohydropyridyl)acetamide; or a solvate, hydrate or pharmaceutically acceptable salt thereof.

29. A compound of claim 1, wherein $R^5$ is a straight or branched chain alkyl of 1 to 12 carbons.

30. A compound of claim 29, wherein said alkyl is selected from the group consisting of methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

31. A compound of claim 1, wherein $R^5$ is cycloalkyl having 3 to 9 carbon atoms.

32. A compound of claim 31, wherein said cycloalkyl is cyclopropyl, cyclobutyl, cyclopentyl, cyclohexyl, cycloheptyl, cyclooctyl or cyclononyl.

33. A compound of claim 1, wherein $R^5$ is aralkyl.

34. A compound of claim 33, wherein said aralkyl comprises a $Cl_{1-6}$ alkyl group and an aryl substituent.

35. A compound of claim 34, wherein said aryl substituent is benzyl, phenylethyl or 2-naphthylmethyl.

36. A pharmaceutical composition for inhibiting proteolysis in a mammal, comprising an amount of a compound of claim 1 effective to inhibit proteolysis, and a pharmaceutically acceptable carrier or diluent.

37. The pharmaceutical composition of claim 36, wherein said compound is present in an effective to inhibit a trypsin-like protease.

38. A method of inhibiting proteolysis in a mammal in need thereof, comprising administering to the mammal the composition of claim 36.

39. The method of claim 38, wherein a trypsin-like protease is inhibited.

40. A process for preparing a compound of claim 1, comprising:

condensing or coupling a compound of formula:

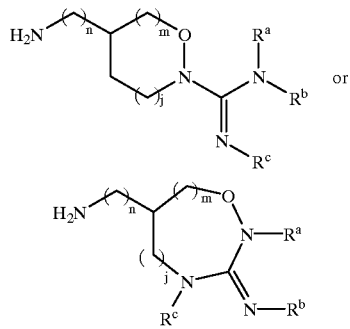

or a salt thereof, with a compound of Formula XI:

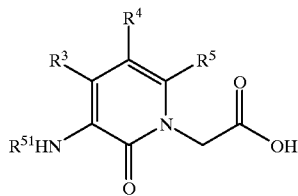

XI where

R$^3$, R$^4$, R$^5$, R$^a$, R$^b$, R$^c$, n, m and j are as defined in claim 1 and where R$^a$, R$^b$, and R$^c$ are optionally protected, and R$^{51}$ is hydrogen or R$^1$—Z—, where R$^1$ and Z are as defined in claim 1; and removing the optional protecting groups if present.

41. The process of claim 40, wherein at least one of R$^a$, R$^b$ and R$^c$ are not hydrogen.

* * * * *

UNITED STATES PATENT AND TRADEMARK OFFICE
CERTIFICATE OF CORRECTION

PATENT NO. : 6,326,492 B1  
DATED : December 4, 2001  
INVENTOR(S) : Aihua Wang et al.

It is certified that error appears in the above-identified patent and that said Letters Patent is hereby corrected as shown below:

Title page,
Item [56], References Cited, FOREIGN PATENT DOCUMENTS, delete duplicate reference "9618644 * 6/1996 (WO)"; delete duplicate reference "9701338 * 6/1996 (WO)";

Column 9,
Line 49, insert the following paragraph: -- Preferred $R^3$ and $R^4$ groups include hydrogen, $C_{1-12}$ alkyl, and $C_{2-6}$ alkenyl. A most preferred value of $R^3$ and $R^4$ is hydrogen. --;

Column 10,
Line 3, delete "2-pyrrolyl" and insert -- 2-pyrolyl --;
Line 4, delete "3-pyrrolyl" and insert -- 3-pyrolyl --;

Column 20,
Line 21, delete "pyitolidinyl" and insert -- pyrrolidinyl --;

Column 27,
Line 21, delete "alinate" and insert -- alginate --;

Column 35,
Line 48, delete "(3methylphenyl)" and insert -- (3-methylphenyl) --;

Column 43,
Line 19, delete "(M=H)" and insert -- , (M+H) --.

Signed and Sealed this

Twenty-third Day of March, 2004

JON W. DUDAS  
*Acting Director of the United States Patent and Trademark Office*